United States Patent
Pratt et al.

(10) Patent No.: US 11,241,338 B2
(45) Date of Patent: Feb. 8, 2022

(54) APPARATUS AND METHODS FOR REGULATING NEGATIVE PRESSURE IN A NEGATIVE PRESSURE WOUND THERAPY SYSTEM

(71) Applicant: KCI Licensing, Inc., San Antonio, TX (US)

(72) Inventors: Benjamin Andrew Pratt, Poole (GB); Michael Bernard Beasley, Wimborne (GB); Christopher Brian Locke, Bournemouth (GB); James Killingworth Seddon, Wimborne (GB)

(73) Assignee: KCI Licensing, Inc., San Antonio, TX (US)

( * ) Notice: Subject to any disclaimer, the term of this patent is extended or adjusted under 35 U.S.C. 154(b) by 941 days.

(21) Appl. No.: 15/766,576

(22) PCT Filed: Nov. 1, 2016

(86) PCT No.: PCT/US2016/059942
§ 371 (c)(1),
(2) Date: Jul. 30, 2018

(87) PCT Pub. No.: WO2017/079174
PCT Pub. Date: May 11, 2017

(65) Prior Publication Data
US 2018/0280202 A1 Oct. 4, 2018

Related U.S. Application Data

(60) Provisional application No. 62/250,430, filed on Nov. 3, 2015.

(51) Int. Cl.
*A61F 13/00* (2006.01)
*A61M 1/00* (2006.01)
(Continued)

(52) U.S. Cl.
CPC ......... *A61F 13/00068* (2013.01); *A61M 1/74* (2021.05); *A61M 1/80* (2021.05);
(Continued)

(58) Field of Classification Search
CPC ..... A61F 13/00068; A61M 1/74; A61M 1/80; A61M 1/90; A61M 2205/3344; A61M 2205/3355
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Tatyana Zalukaeva
*Assistant Examiner* — Jessica R Arble

(57) ABSTRACT

A pressure switch for controlling application of negative pressure to dressing disposed adjacent a tissue site is disclosed. The pressure switch comprises a body having a base, sidewalls extending from the base to an open end, and an inlet coupled to the dressing and forming a passage through the body. The pressure switch further comprises a diaphragm closing the open end of the sidewalls and forming a vacuum chamber with the body, wherein the inlet fluidly couples the (Continued)

vacuum chamber and the dressing. The pressure switch further comprises a valve disposed in the passage and configured to restrict the flow of gas through the passage so that a switch pressure developed in the vacuum chamber as a result of the application of negative pressure to the dressing lags a wound pressure at the tissue site to delay, wherein the diaphragm is adapted to be operatively responsive to the switch pressure to move between a relaxed position and a compressed position as the negative pressure increases and decreases. This pressure switch further comprises a switching element coupled to the diaphragm to turn on the negative pressure in the relaxed position and turn off the negative pressure in the compressed position. In another example, a method for controlling application of negative pressure to dressing disposed adjacent a tissue site using a pressure switch is disclosed. In another example, a system for applying negative pressure to a tissue site using a pressure switch is disclosed.

43 Claims, 16 Drawing Sheets

(51) Int. Cl.
  *H01H 35/24*  (2006.01)
  *H01H 35/34*  (2006.01)
(52) U.S. Cl.
  CPC ............ *A61M 1/90* (2021.05); *H01H 35/245* (2013.01); *H01H 35/34* (2013.01); *H01H 35/346* (2013.01); *A61M 2205/3341* (2013.01); *A61M 2205/3344* (2013.01); *A61M 2205/3355* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |

(56) References Cited

U.S. PATENT DOCUMENTS

| | | | |
|---|---|---|---|
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2007/0032763 | A1 | 2/2007 | Vogel |
| 2010/0063483 | A1* | 3/2010 | Adahan .............. A61M 1/962 604/543 |
| 2011/0092927 | A1* | 4/2011 | Wilkes .............. A61F 13/00059 604/304 |
| 2014/0163491 | A1 | 6/2014 | Schuessler et al. |
| 2015/0080788 | A1 | 3/2015 | Blott et al. |
| 2015/0094674 | A1 | 4/2015 | Pratt et al. |
| 2015/0314092 | A1* | 11/2015 | Kimm .............. A61M 16/0479 128/207.15 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2009016603 A2 | 2/2009 |
| WO | 2016126560 A1 | 8/2016 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A. A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

International Search Report for corresponding PCT/US2016/059942, dated Apr. 1, 2017.

Written Opinion for corresponding PCT/US2016/059942, published May 11, 2017.

\* cited by examiner

APPARATUS AND METHODS FOR REGULATING NEGATIVE PRESSURE IN A NEGATIVE PRESSURE WOUND THERAPY SYSTEM

RELATED APPLICATIONS

This application claims the benefit, under 35 USC 119(e), of the filing of U.S. Provisional Patent Application No. 62/250,430, entitled "Apparatus and Method for Regulating Negative Pressure in a Negative Pressure Wound Therapy System," filed Nov. 3, 2015, which is incorporated herein by reference for all purposes.

TECHNICAL FIELD

The invention set forth in the appended claims relates generally to tissue treatment systems and more particularly, but without limitation, to treating wounds with negative pressure and regulating the negative pressure using an electromechanical regulator having hysteresis capability.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the development and operation of improved therapy systems, components, and processes may benefit healthcare providers and patients.

BRIEF SUMMARY

New and useful systems, apparatuses, and methods for treating wounds with negative pressure and more particularly, but without limitation, to treating wounds by regulating the negative pressure using an electromechanical regulator having hysteresis capability in a negative-pressure therapy environment are set forth in the appended claims. Illustrative embodiments are also provided to enable a person skilled in the art to make and use the claimed subject matter.

Providing negative pressure by a pump to a wound dressing with some hysteresis in the negative pressure reduces the frequency that the pump is turned on during the negative pressure therapy. Running the pump less frequently and reducing the number of on/off cycles reduces audible noise generated by the negative pressure wound therapy system and prolongs battery life in portable negative pressure wound therapy systems that may not have ready access to other power sources.

In some embodiments, negative pressure therapy systems and methods are especially effective for improving tissue granulation when used in conjunction with the application of a regulated negative pressure wherein the negative pressure therapy system includes a pump that provides negative pressure to a wound dressing with some hysteresis. Introducing hysteresis in the negative pressure therapy system reduces the frequency that the pump is turned on during the negative pressure therapy. Running the pump less frequently and reducing the number of on/off cycles reduces audible noise generated by the negative pressure wound therapy system and prolongs battery life in portable negative pressure wound therapy systems that may not have ready access to other power sources. Current systems that may include electronic or software solutions that are designed to include hysteresis may be more complex and costly. Replicating the effects of hysteresis using an electromechanical regulator in a negative pressure wound system is one aspect of the invention described herein.

More specifically, in one example embodiment, a pressure switch for controlling application of negative pressure to dressing disposed adjacent a tissue site is disclosed. The pressure switch may comprise a body having a base, sidewalls extending from the base to an open end, and an inlet coupled to the dressing and forming a passage through the body. The pressure switch may further comprise a diaphragm closing the open end of the sidewalls and forming a vacuum chamber with the body, wherein the inlet fluidly couples the vacuum chamber and the dressing. The pressure switch may further comprise a valve disposed in the passage and configured to restrict the flow of gas through the passage so that a switch pressure developed in the vacuum chamber as a result of the application of negative pressure to the dressing lags a wound pressure at the tissue site to delay, wherein the diaphragm is adapted to be operatively responsive to the switch pressure to move between a relaxed position and a compressed position as the negative pressure increases and decreases. This pressure switch may further comprise a switching element coupled to the diaphragm to turn on the negative pressure in the relaxed position and turn off the negative pressure in the compressed position. In another example embodiment, a method for controlling application of negative pressure to dressing disposed adjacent a tissue site using a pressure switch is disclosed. In another example embodiment, a system for applying negative pressure to a tissue site using a pressure switch is disclosed. The diaphragm may be adapted to be operatively responsive to the switch pressure to move between a relaxed position and a compressed position as the negative pressure increases and decreases. The system may further comprise a switching element coupled to the diaphragm to turn on the negative-pressure source in the relaxed position and turn off the negative-pressure source in the compressed position.

Alternatively, in another example embodiment, a system for applying negative pressure to a tissue site is disclosed and may comprise a dressing including a tissue interface adapted to contact the tissue site and a cover adapted to provide a fluid seal between a therapeutic environment including the tissue interface proximate one side of the cover and a local external environment on the other side of the cover. The system may further comprise a negative-pressure source fluidly coupled to the dressing and adapted to provide negative pressure to the therapeutic environment. The system may further comprise a pneumatic actuator having a body closed by a diaphragm forming a vacuum chamber with the body, an inlet coupled to the dressing and forming a passage through the body to fluidly couple the vacuum chamber and the therapeutic environment, and a valve disposed in the passage and configured to restrict the flow of gas through the passage so that a switch pressure developed in the vacuum chamber as a result of the application of negative pressure lags a wound pressure in the therapeutic environment.

Alternatively, in another example embodiment, a method for controlling application of negative pressure to dressing disposed adjacent a tissue site is disclosed. The method may comprise positioning a dressing including a tissue interface for distributing negative pressure to the tissue site in contact with the tissue site. The method may further comprise coupling a pressure switch to the dressing, the pressure switch having a vacuum chamber and an inlet valve configured to restrict the flow of gas into the vacuum chamber when negative pressure is provided to the tissue interface to develop a switch pressure in the vacuum chamber, wherein the pressure switch operatively responds to the switch pressure to move between a relaxed position and a compressed position as the negative pressure increases and decreases. The method may further comprise providing negative pressure to the tissue interface to generate a wound pressure at the tissue site, and then receiving the negative pressure from the dressing into the vacuum chamber of the pressure switch wherein the switch pressure legs the wound pressure. The method may finally comprise turning on the negative pressure when the pressure switch is in the relaxed position and turning off the negative pressure when the pressure switch is in the compressed position.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
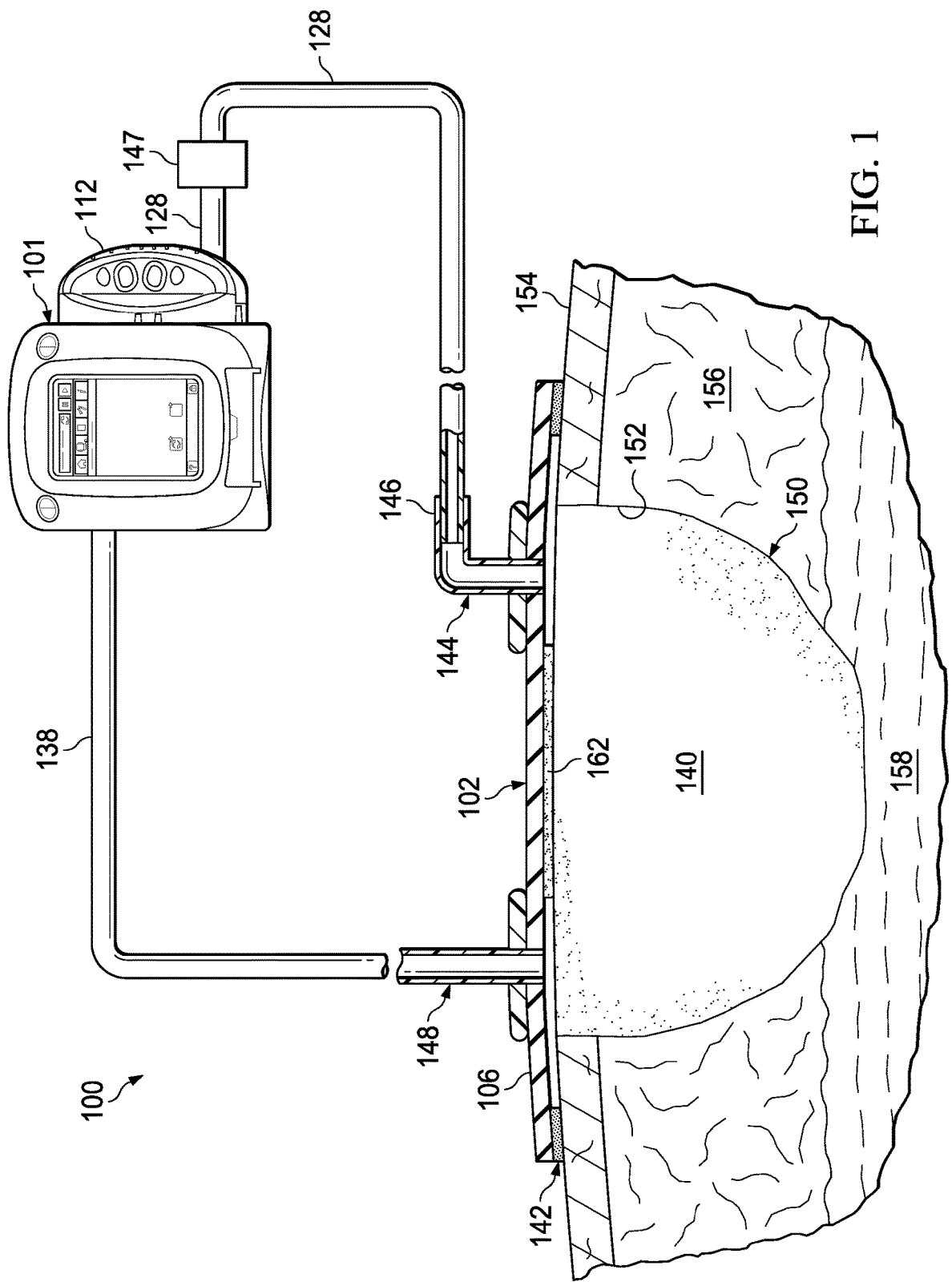
FIG. 1 is a schematic diagram of an example embodiment of a negative-pressure therapy system for delivering negative pressure to a dressing at a tissue site.
Figure 1A:
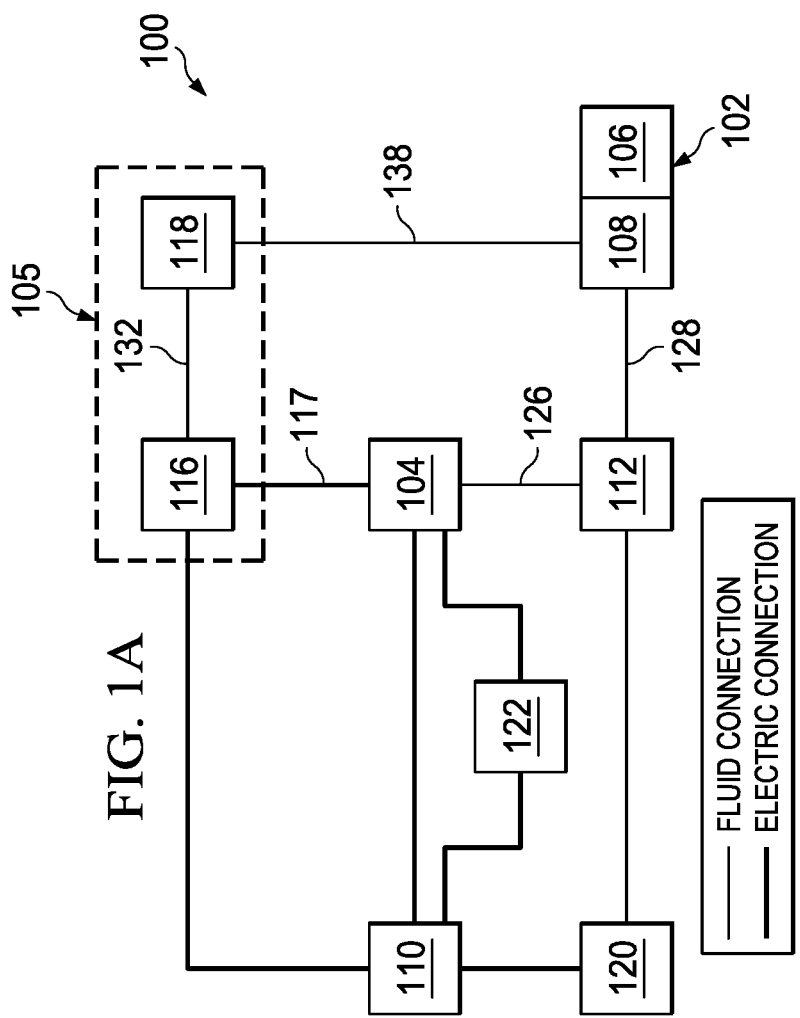
FIG. 1A is a functional block diagram of an example embodiment of a therapy system of FIG. 1 a pump and a first embodiment of pressure switch mechanism having hysteresis capability that can deliver negative pressure in accordance with this specification.

FIG. 1 is a schematic diagram of an example embodiment of a negative-pressure therapy system for delivering treatment solutions to a dressing at a tissue site. FIG. 1A is a simplified functional block diagram of an example embodiment of a therapy system 100 that can provide negative-pressure therapy in accordance with this specification. The therapy system 100 may be packaged in whole or in part as a single, integrated unit such as, for example, therapy apparatus 101. The therapy apparatus 101 may be, for example, a V.A.C.™ Negative Pressure Wound Therapy System available from Kinetic Concepts, Inc. of San Antonio, Tex.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1A, which may include a pump and a motor for driving the pump. A dressing may include a cover, a tissue interface, or both in some embodiments. The dressing 102, for example, may include a cover 106 and a tissue interface 108. A controller, such as a controller 110, may also be coupled to the negative-pressure source 104. The therapy system 100 may optionally include a fluid container, such as a container 112, coupled to the dressing 102 and to the negative-pressure source 104.

The therapy system 100 may also include a pressure switch mechanism 105 that comprises a pressure switch and a pressure regulator. For example, the pressure switch mechanism 105 may include a pressure switch 116 that may be fluidly coupled directly to the dressing 102, as illustrated in the example embodiment of FIG. 1A, or indirectly to the dressing 102 and through the container 112, to measure the pressure at the tissue site, also referred to as the wound pressure (WP). The pressure switch 116 may also be fluidly coupled to the pump of the negative-pressure source 104 to measure the pressure being provided by the pump, also referred to as the pump pressure (PP), as opposed to the wound pressure (WP) which may be less than the pump pressure. The pressure switch 116 may be electrically coupled to the negative-pressure source 104 to switch the negative-pressure source 104 on and off as required by the therapy being applied. The pressure switch 116 may also be electrically coupled to the controller 110 that may be wired or programmed to control the switching of the pressure switch 116 between the on and off states in some example embodiments. A regulator, such as pressure regulator 118, may also be fluidly coupled between the pressure switch 116 and the dressing 102. In some embodiments, the pressure switch 116 and the pressure regulator 118 may be components of a single pressure switch assembly fluidly coupled to the dressing 102.

Additionally, the therapy system 100 may include sensors to measure operating parameters and provide feedback signals to the controller 110 indicative of the operating parameters. As illustrated in FIG. 1A, for example, the therapy system 100 may include a pressure sensor 120, an electric sensor 122, or both, coupled to the controller 110. The pressure sensor 120 may also be coupled or configured to be coupled to a distribution component and to the negative-pressure source 104. The electric sensor 122 may be configured to measure the pressure provided by the negative-pressure source 104, which may be referred to as the pump pressure (PP), and the pressure sensor 120 may be configured to measure the pressure that actually results at the tissue site, which may be referred to as the wound pressure (WP).

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the tissue interface 108 of the dressing 102 through the container 112 by conduits 126 and 128. Additionally, the pressure switch 116 may be directly coupled to the controller 110, and may be indirectly coupled to the tissue interface 108 through the pressure regulator 118 by conduits 132 and 138.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit, such as therapy system 100. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold 140. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of foam may vary according to needs of a prescribed therapy. For example, in some embodiments, the tissue interface 108 may be foam having pore sizes in a range of 400-600 microns. The tensile strength of the tissue interface 108 may also vary according to needs of a prescribed therapy. For example, the tensile strength of foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device, such as an attachment device 142, may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, a dressing interface may facilitate coupling the negative-pressure source 104 to the dressing 102. The negative pressure provided by the negative-pressure source 104 may be delivered through the conduit 128 to a negative-pressure interface 144, which may include an elbow port 146. In one illustrative embodiment, the negative-pressure interface 144 is a T.R.A.C.® Pad or Sensa T.R.A.C.® Pad available from KCI of San Antonio, Tex. The negative-pressure interface 144 allows the negative pressure to be delivered to the cover 106 and realized within an interior portion of the cover 106 and the manifold 140. In this illustrative, non-limiting embodiment, the elbow port 146 extends through the cover 106 to the manifold 140, but numerous arrangements are possible.

The therapy system 100 may also include a particulate filter 147, which may be positioned in fluid communication between the container 112 or the negative-pressure source 104 and the dressing 102. The particulate filter 147 may function to remove particulate matter from the effluent that has circulated through the dressing 102. For example, fluid delivered to the dressing 102 and to a tissue site may be drawn out of the dressing 102 through the negative-pressure interface 144 and transported through conduits 128 to the particulate filter 147. The fluid may be filtered to remove particulate matter in the particulate filter 147, before being recollected in the container 112.

The therapy system 100 may also include a second interface that may facilitate coupling of the pressure switch 116 to the dressing 102, such as pressure interface 148. The pressure sensed by the pressure switch 116 may be delivered through the conduit 138. The pressure interface 148 also may be fluidly coupled to the dressing 102 and may pass through a hole cut in the cover 106. The hole cut in the cover 106 for the pressure interface 148 may be separated as far apart as possible from its location cut in the cover 106 through which the negative-pressure interface 144 may pass. The pressure interface 148 may allow for a fluid to be delivered from the manifold 140 through the cover 106 and to the pressure switch 116.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 122, are generally known in the art as any apparatus operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In operation, the tissue interface 108 may be placed within, over, on, or otherwise proximate to a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can remove exudates and other fluids from the tissue site, which can be collected in container 112.

The tissue site 150 may include, without limitation, any irregularity with a tissue, such as an open wound, surgical incision, or diseased tissue. The therapy system 100 is presented in the context of a tissue site that includes a wound 152, which is through the epidermis 154, or generally skin, and the dermis 156 and reaching into a hypodermis, or subcutaneous tissue 158. The therapy system 100 may be used to treat a wound of any depth, as well as many different types of wounds including open wounds or other tissue sites. The tissue site 150 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 150 may include removal of fluids originating from the tissue site 150, such as exudates or ascites, or fluids instilled into the dressing to cleanse or treat the tissue site 150, such as antimicrobial solutions. The therapy system 100 may be used in broader contexts, including with any type of tissue site including wounds, defects, or other treatment target located on or within living or nonliving tissue.

In one embodiment, controller 110 receives and processes data, such as data related to the pressure distributed to the tissue interface 108 from the pressure sensor 120. The controller 110 may also control the operation of one or more components of therapy system 100 to manage the pressure distributed to the tissue interface 108 for application to the wound 152 at the tissue site 150, the wound pressure (WP). In one embodiment, controller 170 may include an input for receiving a desired target pressure (TP) set by a clinician or other user and may be program for processing data relating to the setting and inputting of the target pressure (TP) to be applied to the tissue site 150. In one example embodiment, the target pressure (TP) may be a fixed pressure value determined by a user/caregiver as the reduced pressure target desired for therapy at the tissue site 150 and then provided as input to the controller 110. The user may be a nurse or a doctor or other approved clinician who prescribes the desired negative pressure to which the tissue site 150 should be applied. The desired negative pressure may vary from tissue site to tissue site based on the type of tissue forming the tissue site 150, the type of injury or wound 152 (if any), the medical condition of the patient, and the preference of the attending physician. After selecting the desired target pressure (TP), the negative-pressure source 104 is controlled to achieve the target pressure (TP) desired for application to the tissue site 150.

Figure 2A:
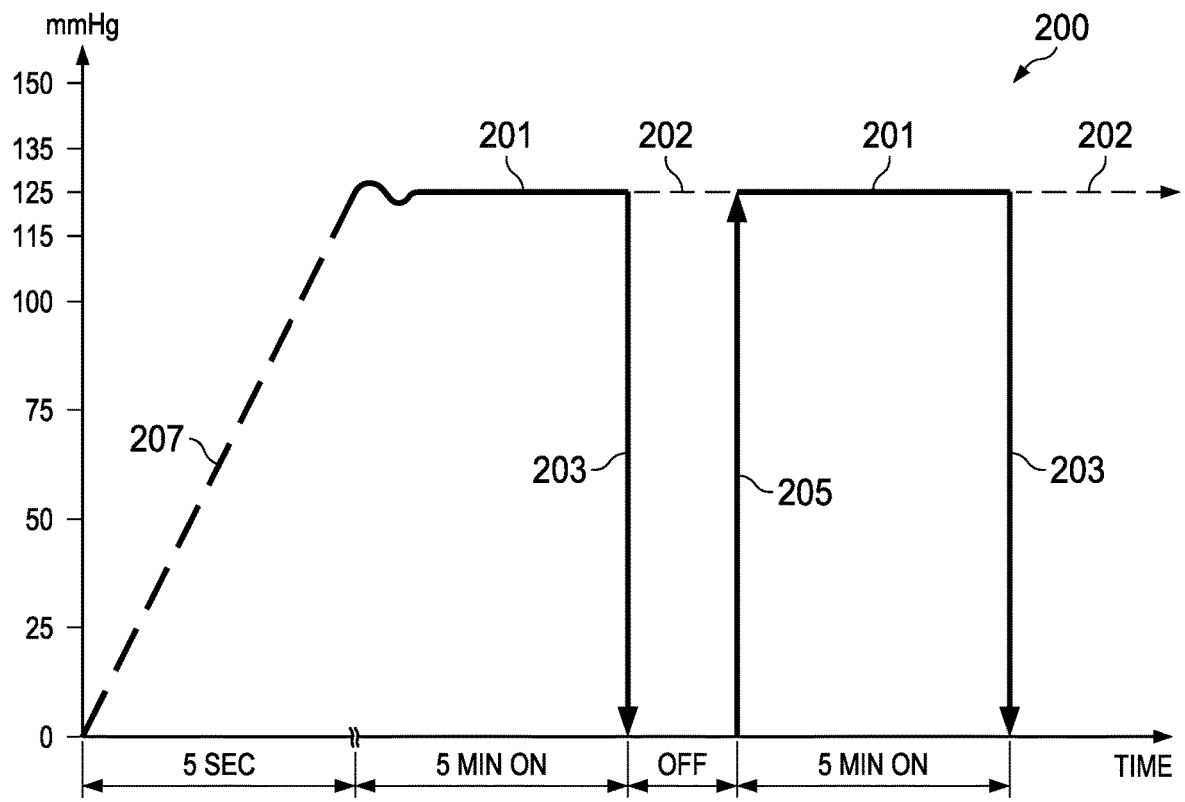
FIG. 2A is a graph illustrating an illustrative embodiment of pressure control modes for the negative-pressure therapy system of FIGS. 1 and 1A wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system.

Referring more specifically to FIG. 2A, a graph illustrating an illustrative embodiment of pressure control modes 200 that may be used for the negative-pressure and instillation therapy system of FIGS. 1 and 1A is shown wherein the x-axis represents time in minutes (min) and/or seconds (sec) and the y-axis represents pressure generated by a pump in Torr (mmHg) that varies with time in a continuous pressure mode and an intermittent pressure mode that may be used for applying negative pressure in the therapy system. The target pressure (TP) may be set by the user in a continuous pressure mode as indicated by lines 201 and dotted line 202 wherein the wound pressure (WP) is applied to the tissue site 150 until the user deactivates the negative-pressure source 104. The target pressure (TP) may also be set by the user in an intermittent pressure mode as indicated by lines 201, 203 and 205 wherein the wound pressure (WP) is cycled between the target pressure (TP) and atmospheric pressure. For example, the target pressure (TP) may be set by the user at 125 mmHg for a specified period of time (e.g., 5 min) followed by the therapy being turned off for a specified period of time (e.g., 2 min) as indicated by line 203 by venting the tissue site 150 to the atmosphere, and then repeating the cycle by turning the therapy back on as indicated by line 205 which consequently forms a square wave pattern between the target pressure (TP) level and no pressure.

The increase of the wound pressure (WP) at the tissue site 150 from ambient pressure to the target pressure (TP) is not instantaneous, but rather gradual depending on the type of therapy equipment and the dressing. For example, the negative-pressure source 104 and the dressing 102 may have an initial rise time as indicated by the dashed line 207 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system 100 is operating in the intermittent mode, the repeating rise time as indicated by line 205 may be a value substantially equal to the initial rise time as indicated by dashed line 207.

The target pressure may also be a variable target pressure (VTP) controlled or determined by controller 110 that varies in a dynamic pressure mode. For example, the variable target pressure (VTP) may vary between a maximum and minimum pressure value that may be set as an input determined by a user as the range of negative pressures desired for therapy at the tissue site 150. The variable target pressure (VTP) may also be processed and controlled by controller 110 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 150.

Figure 2B:
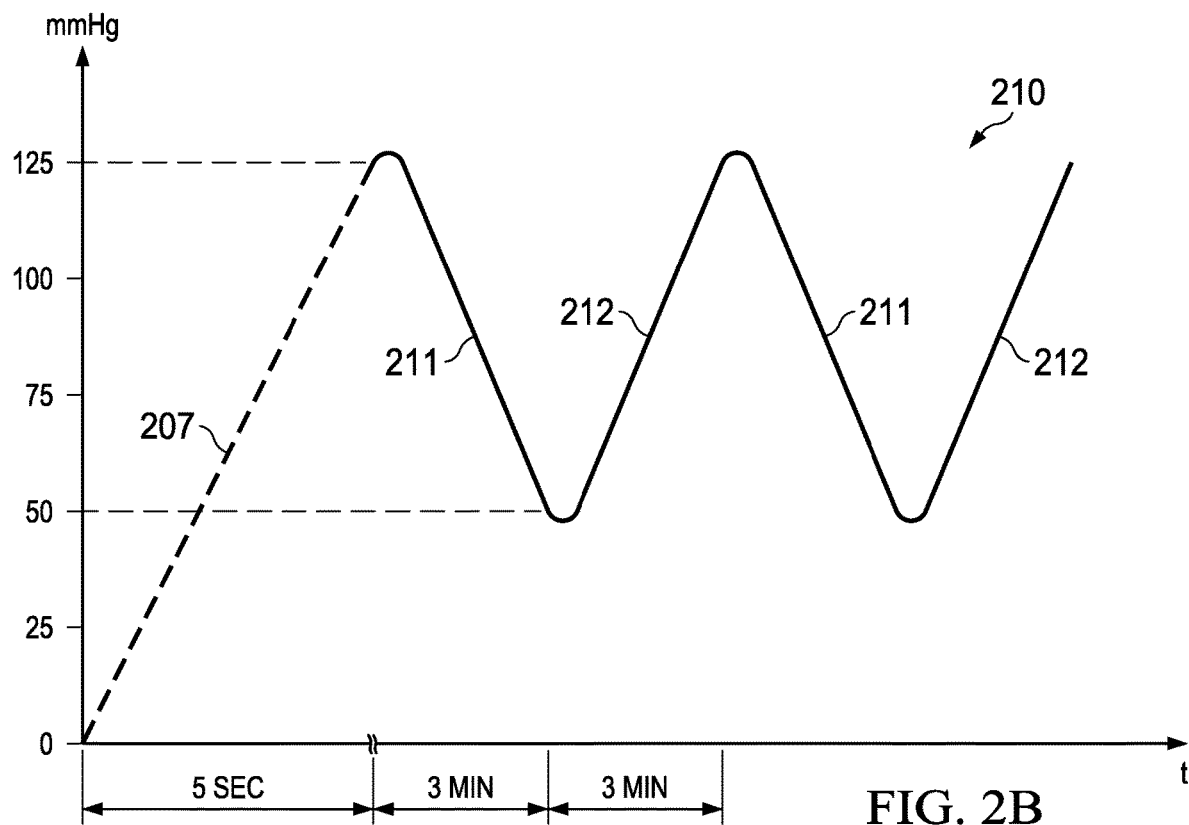
FIG. 2B is a graph illustrating an illustrative embodiment of another pressure control mode for the negative-pressure therapy system of FIGS. 1 and 1A wherein the x-axis represents time in minutes (min) and/or seconds (sec) and the y-axis represents pressure generated by a pump in Torr (mmHg) that varies with time in a dynamic pressure mode that may be used for applying negative pressure in the therapy system.

Referring more specifically to FIG. 2B, a graph illustrating an illustrative embodiment of another pressure control mode for the negative-pressure and instillation therapy system of FIGS. 1 and 1A is shown wherein the x-axis represents time in minutes (min) and/or seconds (sec) and the y-axis represents pressure generated by a pump in Torr (mmHg) that varies with time in a dynamic pressure mode that may be used for applying negative pressure in the therapy system. For example, the variable target pressure (VTP) may be a reduced pressure that provides an effective treatment by applying reduced pressure to tissue site 150 in the form of a triangular waveform varying between a minimum and maximum pressure of 50-125 mmHg with a rise time 212 set at a rate of +25 mmHg/min and a descent time 211 set at −25 mmHg/min, respectively. In another embodiment of the therapy system 100, the variable target pressure (VTP) may be a reduced pressure that applies reduced pressure to tissue site 150 in the form of a triangular waveform varying between 25-125 mmHg with a rise time 212 set at a rate of +30 mmHg/min and a descent time 211 set at −30 mmHg/min. Again, the type of system and tissue site determines the type of reduced pressure therapy to be used.

The application of negative pressure may be implemented to provide a continuous pressure mode of operation as described above to achieve a specific wound pressure (WP) at the tissue interface 108 or a dynamic pressure mode of operation as described above to vary the wound pressure (WP) at the tissue interface 108. Alternatively, the application of negative pressure may be implemented to provide an intermittent mode of operation as described above to save energy and allow the wound pressure (WP) to diminish with any leakage in the tissue interface 108. The controller 110 may be utilized to select any one of these three modes of operation and the duration of the negative pressure therapy as described above. The example embodiments disclosed herein are described as functioning within the framework of a continuous pressure mode of operation, it being understood that these embodiments would function in a similar fashion when utilized in the intermittent or dynamic pressure modes of operation.

Figure 3:
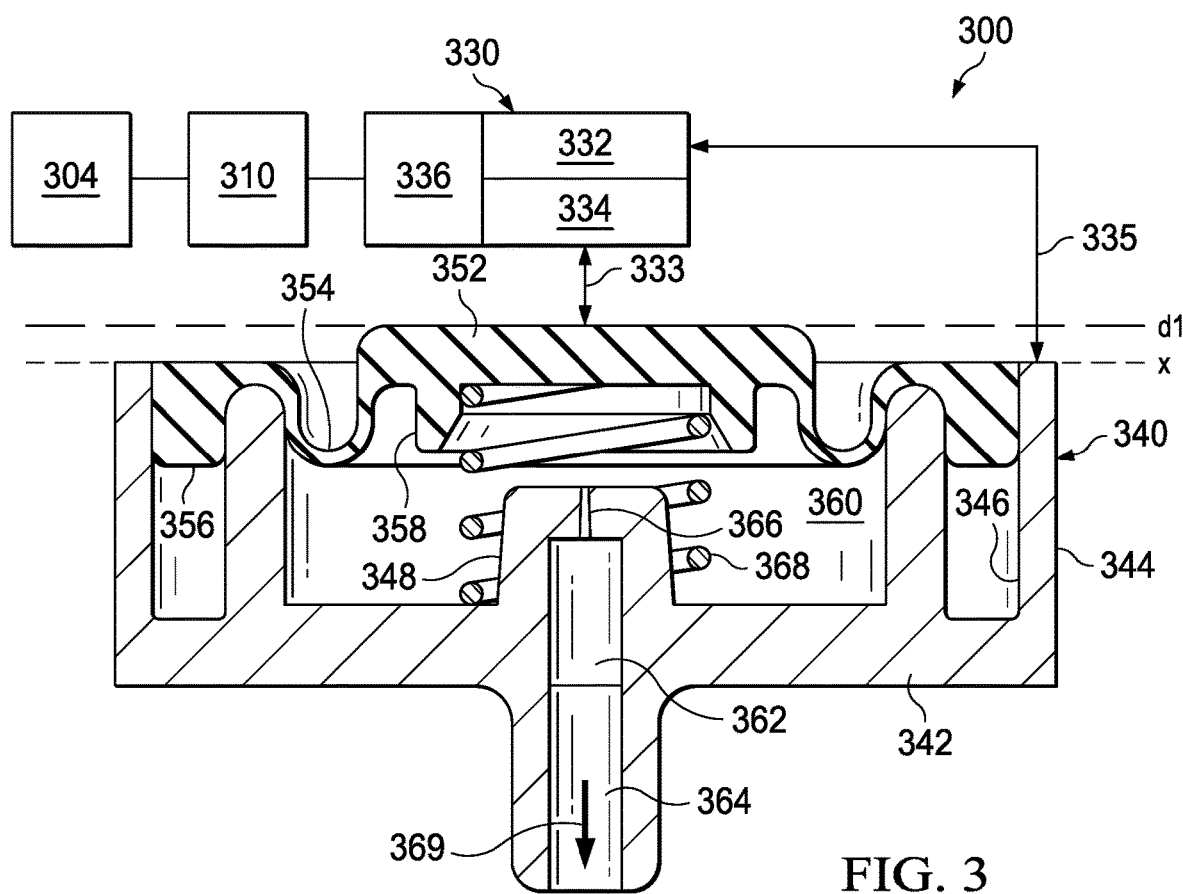
FIG. 3 is a schematic, cross-sectional view of another example embodiment of pressure switch mechanism including a pneumatic actuator and a switching element having hysteresis capability that may be used in the negative pressure therapy system of FIGS. 1 and 1A to deliver negative pressure in accordance with this specification.

FIG. 3 is a schematic, cross-sectional view of another embodiment of pressure switch mechanism 300 that may include a pneumatic actuator 340 and a switching element 330 having hysteresis capability that may be used in the negative pressure therapy system of FIGS. 1 and 1A to deliver negative pressure in accordance with this specification. The switching element 330 may be any electromechanical device that is operatively coupled, directly or indirectly, to a negative-pressure source 304 that may be substantially similar to the negative-pressure source 104 described above. The switching element 330 may turn the negative-pressure source 304 on and off in order to provide a therapeutic negative pressure treatment, directly or indirectly, to a dressing 102 that may be substantially similar to the dressing 102 described above. In one example embodiment, the switching element 330 may be electrically coupled to a controller 310 that may be substantially similar to the controller 110 described above.

The controller 310 also may be configured to control the negative-pressure source 304 by (i) turning the negative-pressure source 304 on in order to initially evacuate the dressing 102 as described above to a maximum target pressure (TPmax) to begin in a continuous mode of operation; (ii) turning the negative-pressure source 304 off when the wound pressure (WP) in the dressing 102 reaches the maximum target pressure (TPmax) and leaving the negative-pressure source 304 off as long as the wound pressure (WP) remains within a desired pressure range (DPR) between the maximum target pressure (TPmax) and a minimum target pressure (TPmin), i.e., the leakage phase; (iii) turning the negative-pressure source 304 back on when the wound pressure (WP) drops below the minimum target pressure (TPmin) as a result of leakage from the system or the dressing 102 and leaving the negative-pressure source 304 on until the wound pressure (WP) reaches the maximum target pressure (TPmax), i.e., the evacuation phase; and (iv) turning the negative-pressure source 304 back off when the wound pressure (WP) reaches the maximum target pressure (TPmax) as set forth in step (ii) to repeat the cycle and continue negative-pressure therapy in a continuous mode of operation. In one example embodiment, the maximum target pressure (TPmax) may be 125 mmHg and the minimum target pressure (TPmin) may be 100 mmHg, so that the desired pressure range (DPR) would be 100-125 mmHg or a pressure bandwidth of 25 mmHg. In another example embodiment, the maximum target pressure (TPmax) may be 150 mmHg and the minimum target pressure (TPmin) may be 50 mmHg, so that the desired pressure range (DPR) would be 50-150 mmHg or a pressure bandwidth of 100 mmHg.

In this illustrative embodiment, the pneumatic actuator 340 may include a base 342, sidewalls 344 having one end supported on the base 342, a diaphragm support 346 having one end supported on the base 342 within the sidewalls 344, and a base spring guide 348 extending from a center portion of the base 342. The pneumatic actuator 340 may further include a diaphragm 350 having a diaphragm membrane 352 forming a center portion of the diaphragm 350 and a peripheral portion extending radially outwardly from the diaphragm membrane 352 and flexibly coupled to the other end of the sidewall 344. In one example embodiment, the peripheral portion may comprise a simple disk shape, flexible material that permits the diaphragm membrane 352 to be movable in a direction generally perpendicular to the surface of the diaphragm membrane 352. In another example embodiment, the peripheral portion may be more complex further comprising a first peripheral portion of the diaphragm 350 extending radially outwardly from the center portion of the diaphragm 350 to provide flexibility, and a second peripheral portion of the diaphragm 350 extending from the first peripheral portion for flexibly attaching the diaphragm 350 to the other end of the sidewalls 344. The first peripheral portion of the diaphragm 350 may have a simple ring shape or may comprise a more complex shape such as, for example, a diaphragm skirt 354 having a U-shape for providing increased flexibility. The second peripheral portion of the diaphragm 350 or the diaphragm skirt 354 may comprise a projection extending generally perpendicularly from the periphery such as, for example, an attachment portion 356 that is tapered to fit snugly between the other end of the sidewall 344 and the other end of the diaphragm support 346 to flexibly support the diaphragm skirt 354. Consequently, the diaphragm membrane 352 may be movable on the diaphragm skirt 354 so that the diaphragm membrane 352 may be displaced toward the base 342 when a vacuum or negative pressure is applied to the diaphragm membrane 352 and away from the base 342 when a positive force is applied against the base 342. Because the attachment portion 356 fits snugly between the sidewall 344 and the diaphragm support 346, the attachment portion 356 also may provide a substantially airtight seal between the diaphragm support 346 and the diaphragm 350. The diaphragm 350 may also comprise a diaphragm connector 358 extending generally perpendicularly from the diaphragm membrane 352 toward the base 342 that may be used to couple the diaphragm membrane 352 to a source of a positive force being applied from the base 342.

The base 342, the diaphragm support 346, the diaphragm membrane 352, and the diaphragm skirt 354 may then form a vacuum chamber 360 that may also include space between the sidewalls 344 and the diaphragm support 346. The base 342 may include a first passageway for fluids such as, for example, a pressure port 362 having a first end for receiving reduced pressure from the dressing 102 and a second end opening into the vacuum chamber 360. A conduit 364 such as, for example, the conduit 138, may fluidly couple the first end of the pressure port 362 to the dressing 102. In one example embodiment, the conduit 364 may extend all the way into the vacuum chamber 360 (not shown) without any obstruction or valve. When negative pressure is applied to the dressing 102, the wound pressure (WP) is also applied via the conduit 364 to the vacuum chamber 360, hereinafter the switch pressure (SP), as indicated by the arrow 369. As a result, the vacuum created in the vacuum chamber 360 begins pulling the diaphragm membrane 352 toward the base 342 when the negative pressure increases to a value that is large enough against a force being applied against the diaphragm membrane 352. The switch pressure (SP) would be substantially equal to the wound pressure (WP) in the evacuation phase as the negative pressure continues to increase or in the leakage phase as the pressure (WP) decreases.

However, the second end of the pressure port 362 opening to the vacuum chamber 360 may also include a valve or any device for controlling the flow of gas through a second passage, e.g., a flow restrictor valve, that restricts the flow of gas into an out of the vacuum chamber 360 creating a pressure differential between the dressing 102 and the vacuum chamber 360. The flow restrictor valve restricts the flow of fluid causing a delay in the amount of time for the switch pressure (SP) to reach either the maximum target pressure (TPmax) or the minimum target pressure (TPmin) after the wound pressure (WP) reaches either one, hereinafter referred to as a restriction time delay Δt. In other words, the switch pressure (SP) does not reach the maximum target pressure (TPmax) in the evacuation phase as quickly as the wound pressure (WP) when negative pressure is being applied to the dressing 102 causing a time delay before the negative-pressure source 304 is turned off, i.e., an off-time delay Δt(off). Correspondingly, the switch pressure (SP) does not reach the minimum target pressure (TPmin) in the leakage phase as quickly as the wound pressure (WP) when negative pressure is leaking from the dressing 102 causing a time delay before the negative-pressure source 304 is turned back on, i.e., an on-time delay Δt(on). (See FIG. 4 and description below.)

This flow restrictor valve introduces hysteresis by slowing the response time of the pressure switch mechanism 300 so that the negative-pressure source 104 runs less frequently to conserve power and reduce noise. The flow of fluid may be restricted by a filter material disposed in the second passage or by simply reducing the diameter of the second passageway compared to the diameter of the first passageway. Hence, in one example embodiment, a flow restrictor valve 366 comprises a second passage with an orifice having a diameter smaller than the diameter of the pressure port 362. The flow restrictor valve 366 reduces fluid flow through the orifice so that the switch pressure (SP) lags behind the wound pressure (WP) whether the wound pressure (WP) is increasing or decreasing as described above. Consequently, movement of the diaphragm membrane 352 is also delayed by the restriction time delay Δt as it moves toward the base 342 with increasing wound pressure (WP), i.e., the off-time delay Δt(off) in the evacuation cycle, and away from the base 342 with decreasing wound pressure (WP), i.e., the on-time delay Δt(on) in the leakage cycle as described in more detail below.

The pneumatic actuator 340 may also include an elastic element disposed between the base 342 and the diaphragm membrane 352 within the vacuum chamber 360. The elastic element may be a spring or other means for storing mechanical energy along with the diaphragm skirt 354 that may also store mechanical energy along with the elastic element. The spring may be a tension spring, a compression spring, a torsion spring, a constant force spring, or a variable force spring. For example, a compression spring may be a coil spring 368 disposed between the base 342 and the diaphragm membrane 352 and that is biased against the diaphragm membrane 352 away from the base 342. The coil spring 368 may be further supported and held in position within the vacuum chamber 360 by the base spring guide 348 that may operatively engage an inner portion at one end of the coil spring 368 and the diaphragm connector 358 that may operatively engage an outer portion at the other end of the coil spring 368. Thus, when negative pressure is applied to the dressing 102, the coil spring 368 compresses longitudinally without slipping transversely within the vacuum chamber 360.

At the commencement of the evacuation phase when the switch pressure (SP) drops below the minimum target pressure (TPmin) because of leakage in the system or the dressing 102 as a result of air leaking back into the dressing 102 and the vacuum chamber 360 in a direction opposite that indicated by the arrow 369, the coil spring 368 may be fully extended in a relaxed position along with the diaphragm membrane 352. When negative pressure is again applied to the dressing 102 to overcome the leakage and the switch pressure (SP) rises back above the minimum target pressure (TPmin) towards the maximum target pressure (TPmax), the switch pressure (SP) begins pulling the diaphragm membrane 352 back toward the base 342 against the force being applied by the coil spring 368 causing the coil spring 368 to compress and move along with the diaphragm membrane 352 toward a fully compressed position. At the commencement of the leakage phase when the switch pressure (SP) reaches the maximum target pressure (TPmax), the coil spring 368 is compressed in the fully compressed position along with the diaphragm membrane 352. The distance traveled by the coil spring 368 and the diaphragm membrane 352 from the relaxed position to the fully compressed position is referred to as the displacement (d). The displacement (d) may be increased or decreased to increase or decrease, respectively, the maximum target pressure (TPmax). Correspondingly, the displacement (d) may be increased or decreased to decrease or increase, respectively the minimum target pressure (TPmin). Consequently, the desired pressure range (DPR) of operation may be increased or decreased by increasing or decreasing the displacement (d) of the coil spring 368. The spring constant of the coil spring 368 also may be increased or decreased to adjust the displacement (d) of the coil spring 368.

The switching element 330 may have an actuator portion 332 having a fixed or movable position relative to the position of the pneumatic actuator 340 as indicated by the bidirectional arrow 333. The switching element 330 also may have diaphragm portion 334 having a fixed or movable position relative to the position of the diaphragm 350 as indicated by the bidirectional arrow 335. The movable position in both cases means a variable position having a known displacement with respect to the pneumatic actuator 340 and/or the diaphragm 350. The diaphragm portion 334 of the switching element 330 may be operatively coupled, either directly or indirectly, to the coil spring 368, so that the diaphragm portion 334 moves between the relaxed position and the fully compressed position as indicated by the bidirectional arrow 333 to provide at least one switching signal (S) at each position. As indicated above, travel between these two positions provides an indication of the displacement (d) of the coil spring 368 and/or the diaphragm 350 as a result of negative pressure being applied to the dressing 102 or leaking from the dressing 102.

Figure 3A:
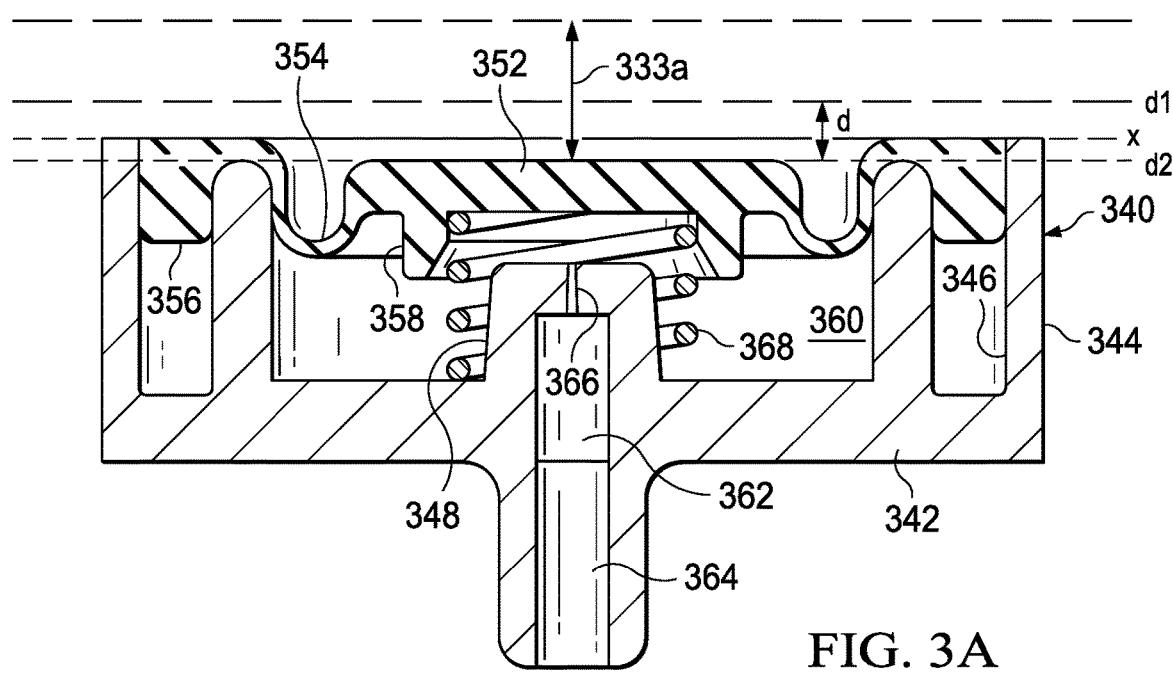
FIGS. 3A-3C are schematic, cross-sectional views of the pneumatic actuator of the pressure switch mechanism of FIG. 3 in a compressed state, a neutral state, and a relaxed state, respectively.
Figure 3B:
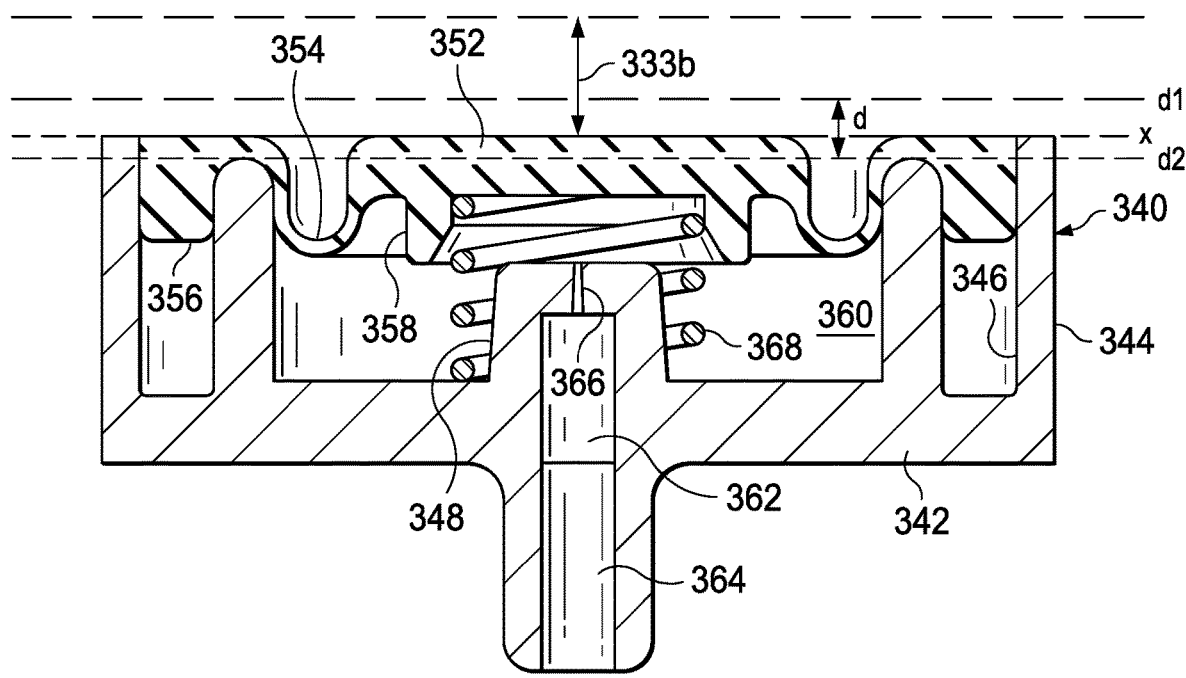
Figure 3C:
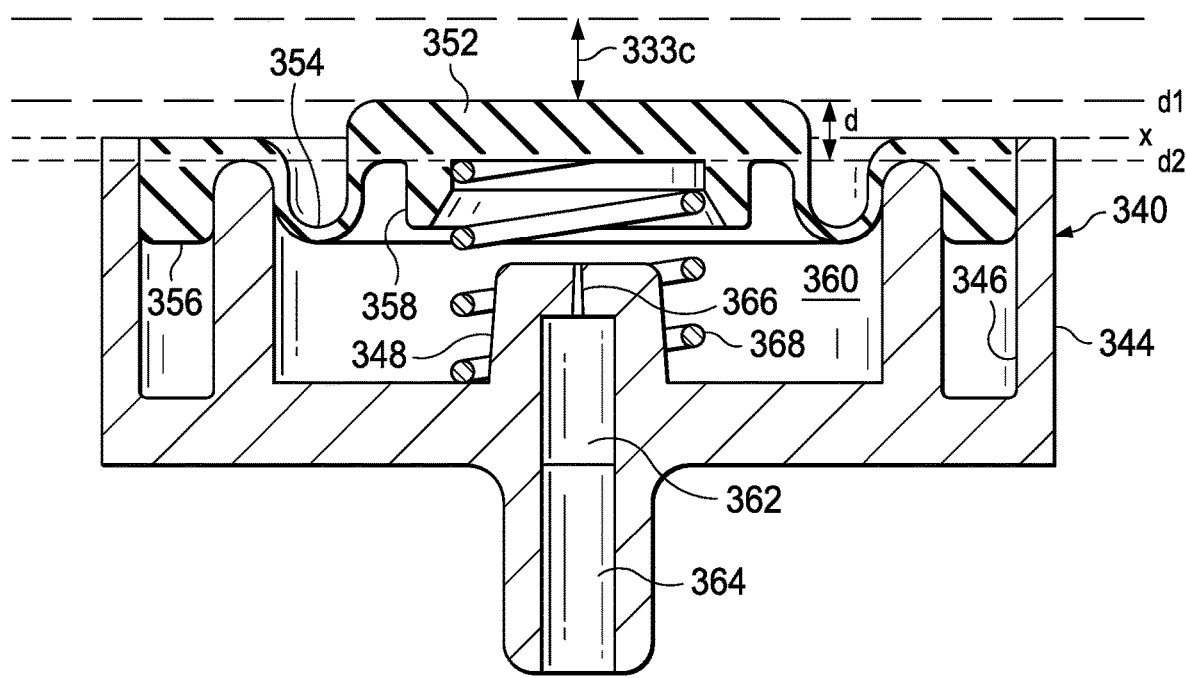

Referring now to FIGS. 3 and 3A-3C, the diaphragm portion 334 of the switching element 330 moves between a relaxed position (d1) and a fully compressed position (d2) as indicated by the bidirectional arrows 333c and 333a, respectively, with respect to a fixed position of the actuator portion 332 as indicated by the bidirectional arrow 335 in FIG. 3 and a dashed reference line (x) in FIGS. 3A-3C. The diaphragm portion 334 moves between the relaxed position (d1) and the fully compressed position (d2) through a neutral range of positions corresponding to the neutral state of the coil spring 368 as indicated by the bidirectional arrow 333b in FIG. 3B. In the evacuation phase, the diaphragm portion 334 of the switching element 330 may be displaced from the relaxed position (d1) as indicated by the bidirectional arrow 333c as shown in FIGS. 3 and 3C, corresponding to a relaxed state of the coil spring 368, toward the fully compressed position (d2) as indicated by the bidirectional arrow 333a shown in FIG. 3A, corresponding to a compressed state of the coil spring 368. Thus, as the diaphragm portion 334 increases the displacement (d) while moving through the neutral range of positions as indicated by the bidirectional arrow 333b shown in FIG. 3B when the coil spring 368 compresses. In the leakage phase, the diaphragm portion 334 of the switching element 330 may be displaced in the opposite direction, or upwardly, from the fully compressed position (d2) as indicated by the bidirectional arrow 333a shown in FIG. 3A, corresponding to a compressed state of the coil spring 368, toward the relaxed position (d1) as indicated by the bidirectional arrow 333c shown in FIG. 3C, corresponding to a relaxed state of the coil spring 368. Thus, the diaphragm portion 334 decreases displacement (d) while moving through the neutral range of positions as indicated by the bidirectional arrow 333b shown in FIG. 3B when the coil spring 368 decompresses.

The switching element 330 may provide the switching signal (S) alternately at the relaxed position (d1) when the coil spring 368 is in the relaxed state to provide a first switching signal (S1) and at the fully compressed position (d2) when the coil spring 368 is in the compressed state to provide a second switching signal (S2), but no switching signal (S) in the neutral state. The switching element 330 may include a switching module 336 that turns the negative-pressure source 304 on and off via the controller 310 in response to the switching signal (S) that toggles between the first switching signal (S1) and the second switching signal (S2). The switching module 336 may be electronic circuitry or software that may be a portion of or stored on the controller 310 or the pressure switch mechanism 300. The switching signals (S) may be any type of signal such as, for a low or high digital signal, depending on the type of switching module 336 being utilized. For example, the electronic circuitry may be a T-type flip-flop that changes states between the relaxed state and the compressed state whenever its clock input is strobed by the switching signal (S), which alternates between the first switching signal (S1) that turns on the negative-pressure source 304 in the relaxed state and the second switching signal (S2) the turns off the negative-pressure source 304 and the compressed state, but holds the previous state value during the intermediate neutral state when no switching signal (S) is being provided to the clock input.

Figure 4:
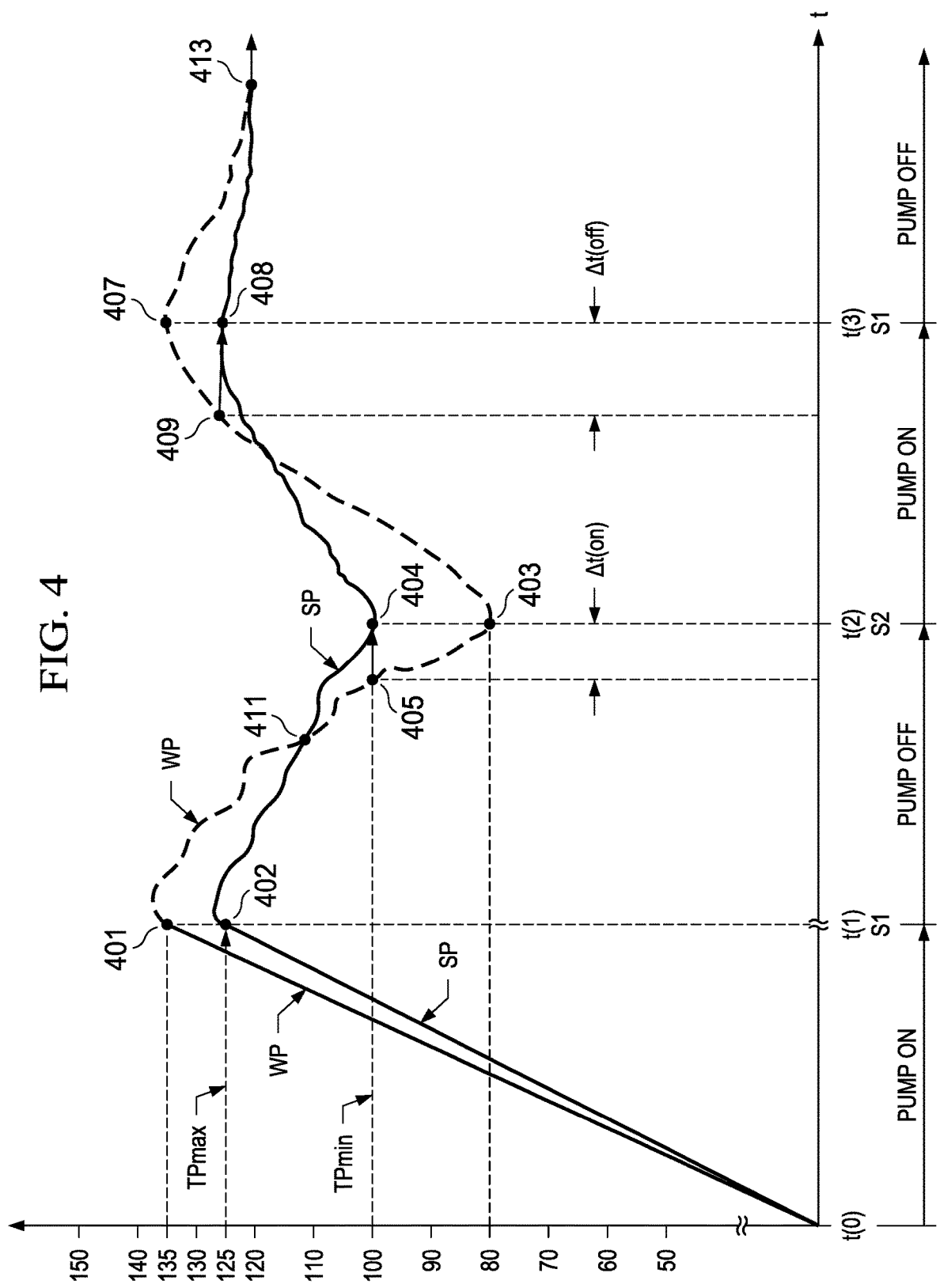
FIG. 4 is a graph illustrating the state change of the pressure switch mechanism of FIGS. 3 and 3A-3C, and a graph illustrating the wound pressure at a tissue site and the corresponding pressure within the pressure switch mechanism, wherein the x-axis represents time in minutes and/or seconds and the y-axis represents pressure in Torr (mmHg) that varies with time.

The controller 310 also may be configured to control the negative-pressure source 304 as described above and, more specifically, in response to the switching signal (S) provided by the switching module 336. Referring now to FIG. 4 in conjunction with FIGS. 3A-3B and assuming for this example embodiment that the pressure port 362 does not include the flow restrictor 366 so that the switch pressure (SP) is substantially equal to the wound pressure (WP) as represented by the solid reference line SP, a caregiver or patient may turn on the negative-pressure source 304 in order to initially evacuate the dressing 102 as described above to a maximum target pressure (TPmax) to begin a continuous mode of operation. When the switch pressure (SP) reaches the maximum target pressure (TPmax) at 402, i.e., SP≥TPmax, causing the pneumatic actuator 340 to collapse into the compressed state (FIG. 3A), the switching module 336 provides the first switching signal (S1) at time t(1) that turns off the negative-pressure source 304 to commence the leakage phase, and leaves the negative-pressure source 304 off in the neutral state as long as the switch pressure (SP) remains within the desired pressure range (DPR) between the maximum target pressure (TPmax) and the minimum target pressure (TPmin), i.e., TPmin<SP<TPmax. When the switch pressure (SP) drops down to or below the minimum target pressure (TPmin) at 404 because the negative pressure is leaking from the system or the dressing 102, i.e., SP≤TPmin, causing the pneumatic actuator 340 to expand into the relaxed state (FIG. 3C), the switching module 336 provides the second switching signal (S2) at time t(2) that turns on the negative-pressure source 304 to commence the evacuation phase, and leaves the negative-pressure source 304 on in the neutral state until the switch pressure (SP) again reaches the maximum target pressure (TPmax). When the switch pressure (SP) reaches the maximum target pressure (TPmax) at 408 causing the pneumatic actuator 340 to collapse again into the compressed state (FIG. 3A), the switching module 336 provides the first switching signal (S1) again at time t(3) that turns off the negative-pressure source 304 to commence the leakage phase as set forth above to repeat the cycle and continue negative-pressure therapy in a continuous mode of operation. In this example embodiment shown in FIG. 4, the maximum target pressure (TPmax) may be 125 mmHg and the minimum target pressure (TPmin) may be 100 mmHg, so that the desired pressure range (DPR) would be 100-125 mmHg or a pressure bandwidth of 25 mmHg.

In another example embodiment where the pressure port 362 does include the flow restrictor 366, the switch pressure (SP) does not necessarily equal the wound pressure (WP) represented by the dashed reference line WP, because the switch pressure (SP) legs by the restriction time delay Δt with increasing wound pressure (WP), i.e., the on-time delay Δt(off), and with decreasing wound pressure (WP), i.e., restriction time delay Δt(on), as described above. In this embodiment, a caregiver or patient may turn on the negative-pressure source 304 in order to initially evacuate the dressing 102 as described above to a maximum target pressure (TPmax), but the switch pressure (SP) would not reach the maximum target pressure (TPmax) as quickly as the wound pressure (WP) because the switch pressure (SP) lags the wound pressure (WP) causing a time delay before the negative-pressure source 304 is actually turned off, i.e., the off-time delay Δt(off), as described above. Consequently, the wound pressure (WP) may rise to an upper peak pressure at 401 during this restriction time delay that is larger than the maximum target pressure (TPmax), e.g. 135 mmHg.

When the switch pressure (SP) does reach the maximum target pressure (TPmax) at time t(1), the negative-pressure source 304 is turned off commencing the leakage phase as described above. Correspondingly, the switch pressure (SP) does not drop down to or below the minimum target pressure (TPmin) as quickly as the wound pressure (WP) does at 405 when negative pressure is leaking from the dressing 102 because the switch pressure (SP) lags the wound pressure (WP) causing an on-time delay Δt(on) before the switch pressure (SP) reaches the minimum target pressure (TPmin) at 404 to turn on the negative-pressure source 304. When the switch pressure (SP) does drop down to or below the minimum target pressure (TPmin) at time t(2), the negative-pressure source 304 is turned back on commencing the evacuation phase as described above at which point the wound pressure (WP) may drop down to or below a lower peak pressure at 403 during this restriction time delay that is less than the minimum target pressure (TPmin), e.g., 80 mmHg. As the wound pressure (WP) increases, the switch pressure (SP) again does not reach the maximum target pressure (TPmax) as quickly as the wound pressure (WP) does at 409 causing an off-time delay Δt(off) before the switch pressure (SP) reaches the maximum target pressure (TPmax) at 408 to turn on the negative-pressure source 304. When the switch pressure (SP) does reach the maximum target pressure (TPmax) at time t(3), the negative-pressure source 304 is again turned off commencing the leakage phase as described above at which point the wound pressure (WP) may rise to another upper peak pressure at 407 that is greater than the maximum target pressure (TPmax). When the switch pressure (SP) reaches the maximum target pressure (TPmax) at 408, the switching module 336 again turns off the negative-pressure source 304 to repeat the cycle and continue negative-pressure therapy in a continuous mode of operation.

During the continuous mode of operation, negative pressure may leak from the dressing 102 or the system at different rates, i.e., leakage rates, that may be greater or less than the restriction time delay Δt described above. In one example embodiment where the dressing initially may have a significant leak, the leakage rate may be greater than the restriction time delay Δt such that the wound pressure (WP) is greater than the switch pressure (SP) at the time t(1) and drops quickly below the switch pressure (SP) at 411 down to the lower peak pressure at the time t(2) as shown in FIG. 4. In another example embodiment where the dressing may have been readjusted to reduce the leak, the leakage rate may be less than the restriction time delay Δt such that the wound pressure (WP) is initially greater than the switch pressure (SP) at the time t(3), but drops more slowly so that the switch pressure (SP) actually catches up with the wound pressure (WP) at 413 and remains in the desired pressure range (DPR) between the maximum target pressure (TPmax) and the minimum target pressure (TPmin) after the time t(3).

Fundamentally, the flow restrictor 366 introduces hysteresis by slowing the response time of the pressure switch mechanism 300 so that the negative-pressure source 104 runs less frequently to conserve power and reduce noise. The flow restrictor 366 reduces fluid flow through the orifice so that the switch pressure (SP) lags behind the wound pressure (WP) whether the wound pressure (WP) is increasing or decreasing as described above. Consequently, movement of the diaphragm membrane 352 is also delayed by the restriction time delay Δt as it moves toward the base 342 with increasing wound pressure (WP), i.e., the off-time delay Δt(off), and away from the base 342 with decreasing wound pressure (WP), i.e., the on-time delay Δt(on).

The switching element 330 may be any electromechanical device that is operatively coupled, either directly or indirectly, to the diaphragm membrane 352 of the pneumatic actuator 340 and also may include the actuator portion 332 and the diaphragm portion 334 as described above. In one example embodiment, the switching element 330 including the actuator portion 332 and the diaphragm portion 334 may be a single-pole, double-throw (SPDT) electromechanical switch shown as switching element 530 in FIG. 5 including an actuator portion 532 and a diaphragm portion 534 that function in a substantially similar fashion as described above. The actuation portion 532 may include an electrical contact that has two ends, a first end 531 in a fixed position relative to the position of the pneumatic actuator 340 as indicated by the bidirectional arrow 535 and the dashed reference line (x), and a second opposite end that may have a contact tip 533 that provides electrical contact. The diaphragm portion 534 may include an electrical contact having a cross-sectional shape of an I-beam with two flanges, a first flange 536 of which is mechanically coupled to the diaphragm membrane 352 in a fixed relationship with the position of the diaphragm membrane 352, and a second flange 538 opposite the first flange 536. The first flange 536 and the second flange 538 provide electrical contacts of the diaphragm portion 534 that move together with the diaphragm membrane 352 between the relaxed position and the fully compressed position as described above. The contact tip 533 of the actuator portion 532 extends into the space between the flanges of the diaphragm portion 534 to provide at least one switching signal (S) when contacting either flange, the first flange 536 at the relaxed and the second flange 538 at the fully compressed positions. As indicated above, travel between these two positions provides an indication of the displacement (d) of the coil spring 368 and/or the diaphragm 350 as a result of negative pressure being applied to the dressing 102 or leaking from the dressing 102.

Figure 5:
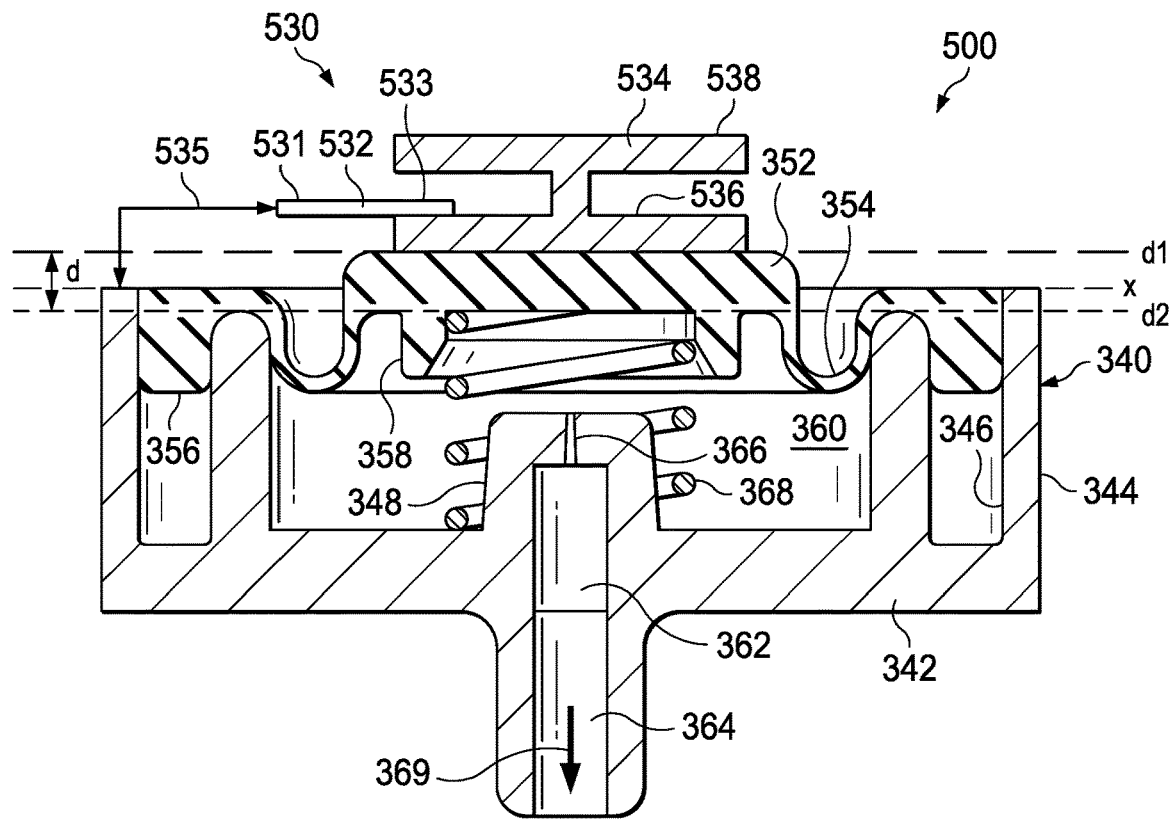
FIG. 5 is a schematic, cross-sectional view of a first embodiment of the pressure switch mechanism of FIG. 3 including the pneumatic actuator and a first example embodiment of a switching element comprising a single-pole, double-throw (SPDT) electromechanical switch to deliver negative pressure in accordance with this specification.
Figure 5A:
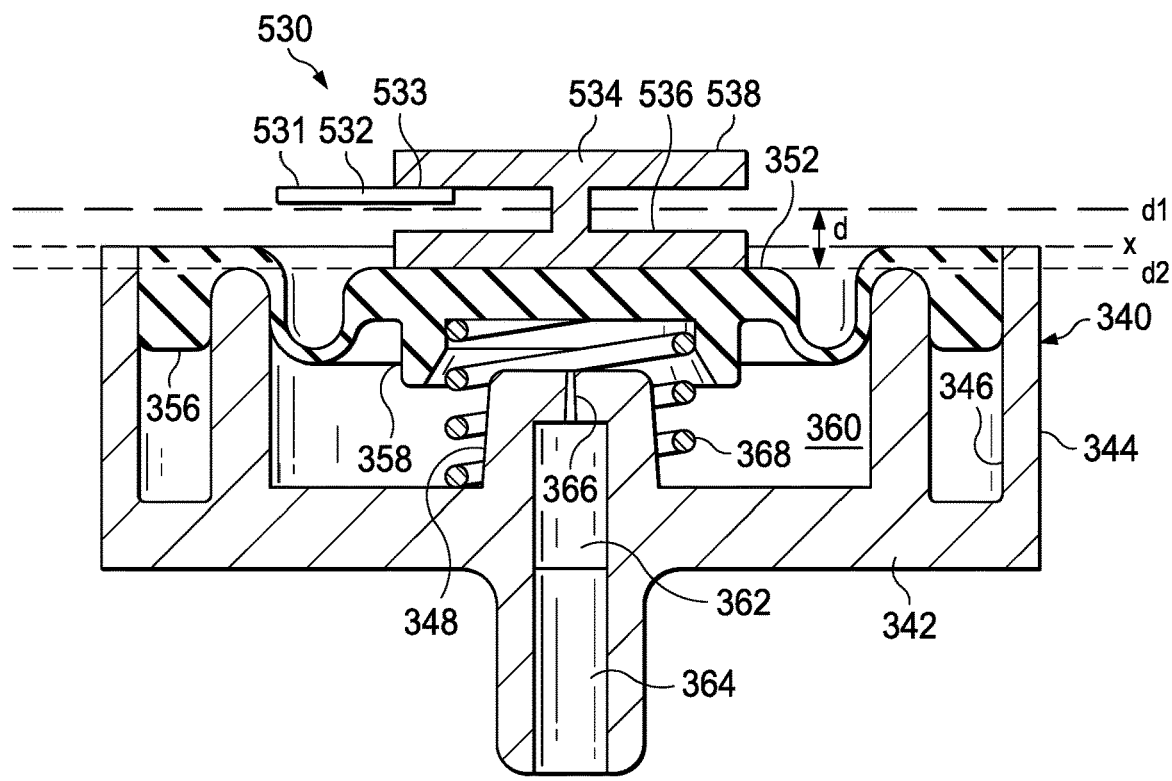
FIGS. 5A-5C are schematic, cross-sectional views of the pneumatic actuator of the pressure switch mechanism of FIG. 5 in a compressed state, a neutral state, and a relaxed state, respectively.
Figure 5B:
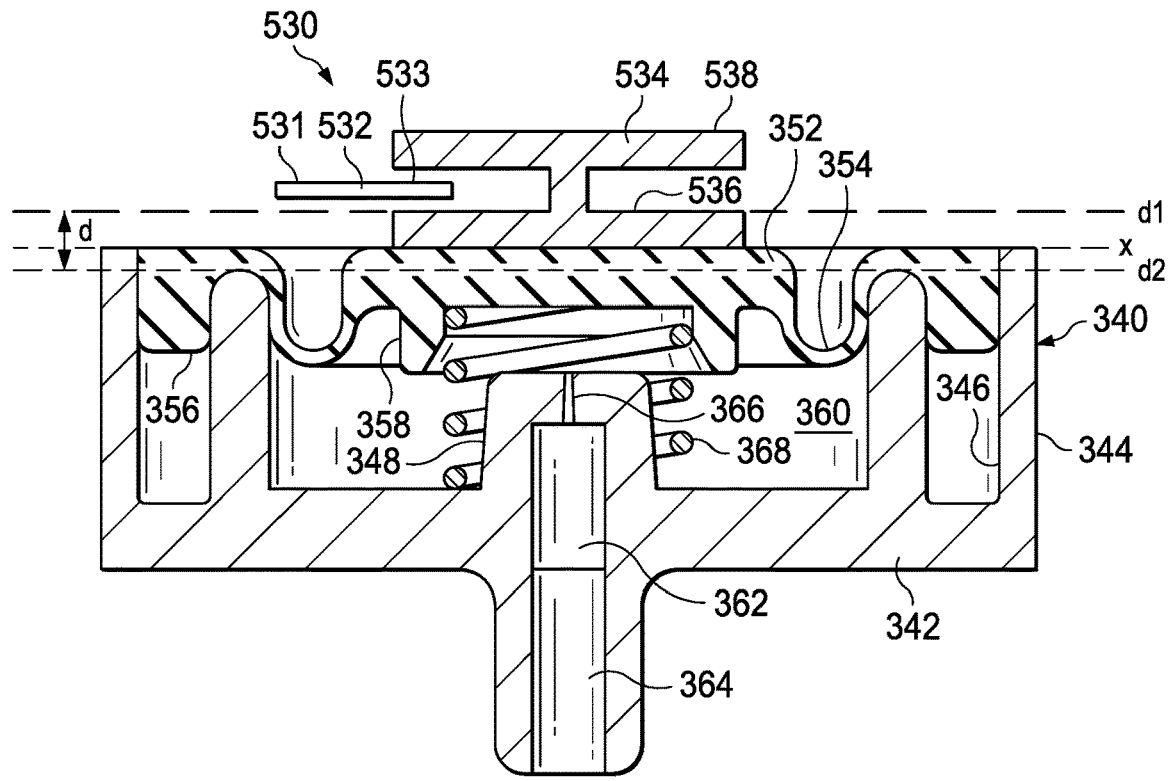
Figure 5C:
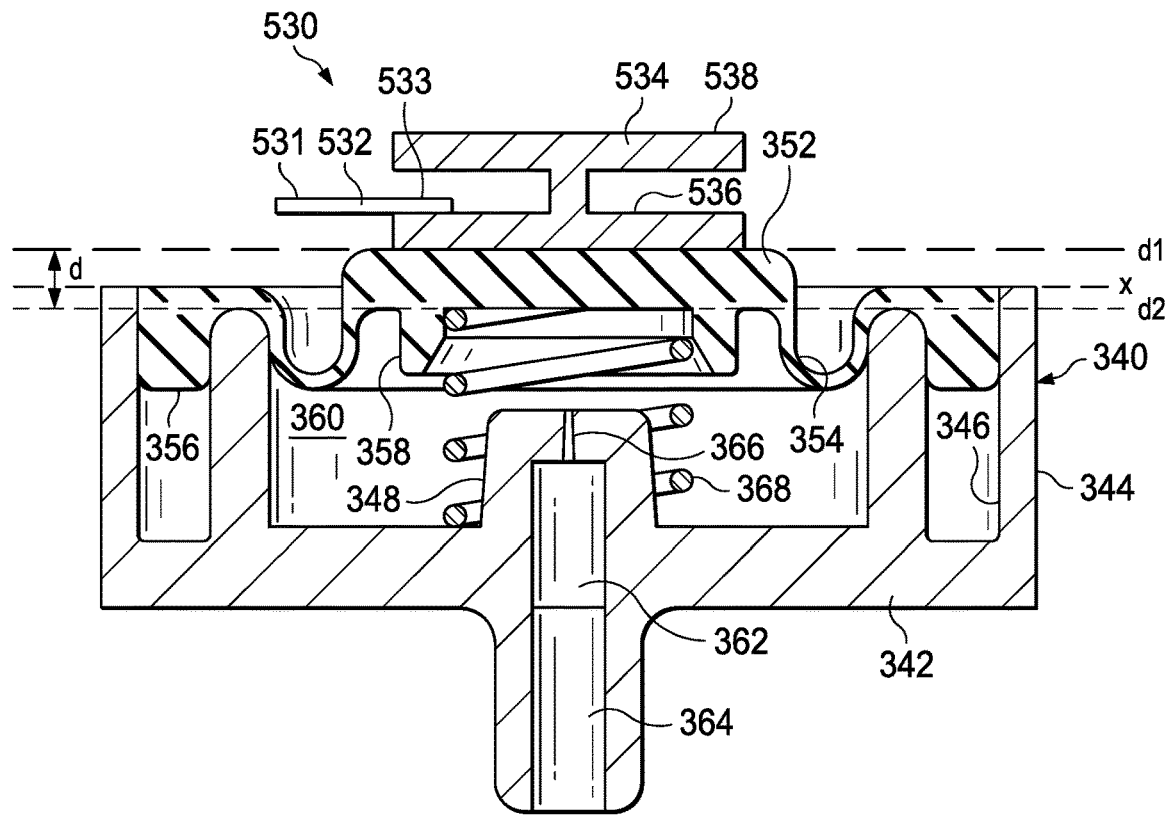

Referring now to FIGS. 5 and 5A-5C, the diaphragm portion 534 of the switching element 430 moves between a relaxed position (d1) and a fully compressed position (d2) as shown in FIGS. 5C and 5A, respectively, with respect to a fixed position of the actuator portion 332 as indicated by the bidirectional arrow 535 in FIG. 5 and a dashed reference line (x) in FIGS. 5A-5C. The diaphragm portion 534 moves between the relaxed position (d1) and the fully compressed position (d2) through a neutral range of positions corresponding to the neutral state of the coil spring 368 as shown in FIG. 5B. More specifically, the diaphragm portion 534 of the switching element 530 may be displaced from the relaxed position (d1) as shown in FIG. 5C, corresponding to a relaxed state of the coil spring 368, toward the fully compressed position (d2) as shown in FIG. 5A, corresponding to a compressed state of the coil spring 368. Thus, the diaphragm portion 534 increases the displacement (d) while moving through the neutral range of positions as shown in FIG. 5B when the coil spring 368 compresses. When the diaphragm portion 534 reaches the fully compressed position (d2), the upper portion of the contact tip 533 makes electrical contact with the second flange 538 of the diaphragm portion 534 as shown in FIG. 5A. This displacement occurs when negative pressure is applied to the dressing 102 and the tissue site 150 as describe above.

When negative pressure leaks from the dressing 102 and the tissue site 150 and the switch pressure (SP) reaches the minimum target pressure (TPmin) as a result of the leaks as describe above, the diaphragm portion 534 begins moving toward the relaxed position (d1). The diaphragm portion 534 of the switching element 530 may be displaced in the opposite direction, or upwardly, from the fully compressed position (d2) as shown in FIG. 5A, corresponding to a compressed state of the coil spring 368, toward the relaxed position (d1) as shown in FIGS. 5 and 5C, corresponding to a relaxed state of the coil spring 368. Thus, the diaphragm portion 534 decreases displacement (d) while moving through the neutral range of positions as shown in FIG. 5B when the coil spring 368 decompresses. When the diaphragm portion 534 reaches the relaxed position (d1), the lower portion of the contact tip 533 makes electrical contact with the first flange 536 of the diaphragm portion 534 as shown in FIGS. 5 and 5C.

The switching element 530 may provide the switching signal (S) alternately between the relaxed position (d1) when the coil spring 368 is in the relaxed state to provide a first switching signal (S1) and the fully compressed position (d2) when the coil spring 368 is in the compressed state to provide a second switching signal (S2), but no switching signal (S) in the neutral state. When the diaphragm portion 534 reaches the fully compressed position (d2) as described above, the upper portion of the contact tip 533 makes electrical contact with the second flange 538 of the diaphragm portion 534 as shown in FIG. 5A to close the circuit and provide the second switching signal (S2). Correspondingly, when the diaphragm portion 534 reaches the relaxed position (d1) as described above, the lower portion of the contact tip 533 makes electrical contact with the first flange 536 of the diaphragm portion 534 as shown in FIGS. 5 and 5C to close the circuit and provide the first switching signal (S1). The switching element 530 also may include a switching module substantially similar to the switching module 336 described above that turns the negative-pressure source 304 on and off via the controller 310 in response to the switching signal (S) that toggles between the first switching signal (S1) and the second switching signal (S2), both of which are closed circuit signals, while the signal (S) is open circuit at all other positions in the neutral state. The switching element 530 may provide the switching signals (S) to the switching module 336 fashion similar to that set forth in Table I.

TABLE I

| State of System | Diaphram Position | Switching Element | Switching Signals(s) |
| --- | --- | --- | --- |
| Start evacuation | Relaxed | Open | 1-0 |
| Evacuating | Neutral | Stays open | 0 |
| Pump off (Tmax) | Compressed | Closes | S2:0-1 |
| Steady State | Neutral | Opens after closing | 0 |
| Pump on (Tmin) | Relaxed | Closes | S1:0-1 |
| Evacuating | Neutral | Opens after closing | 0 |

Figure 6:
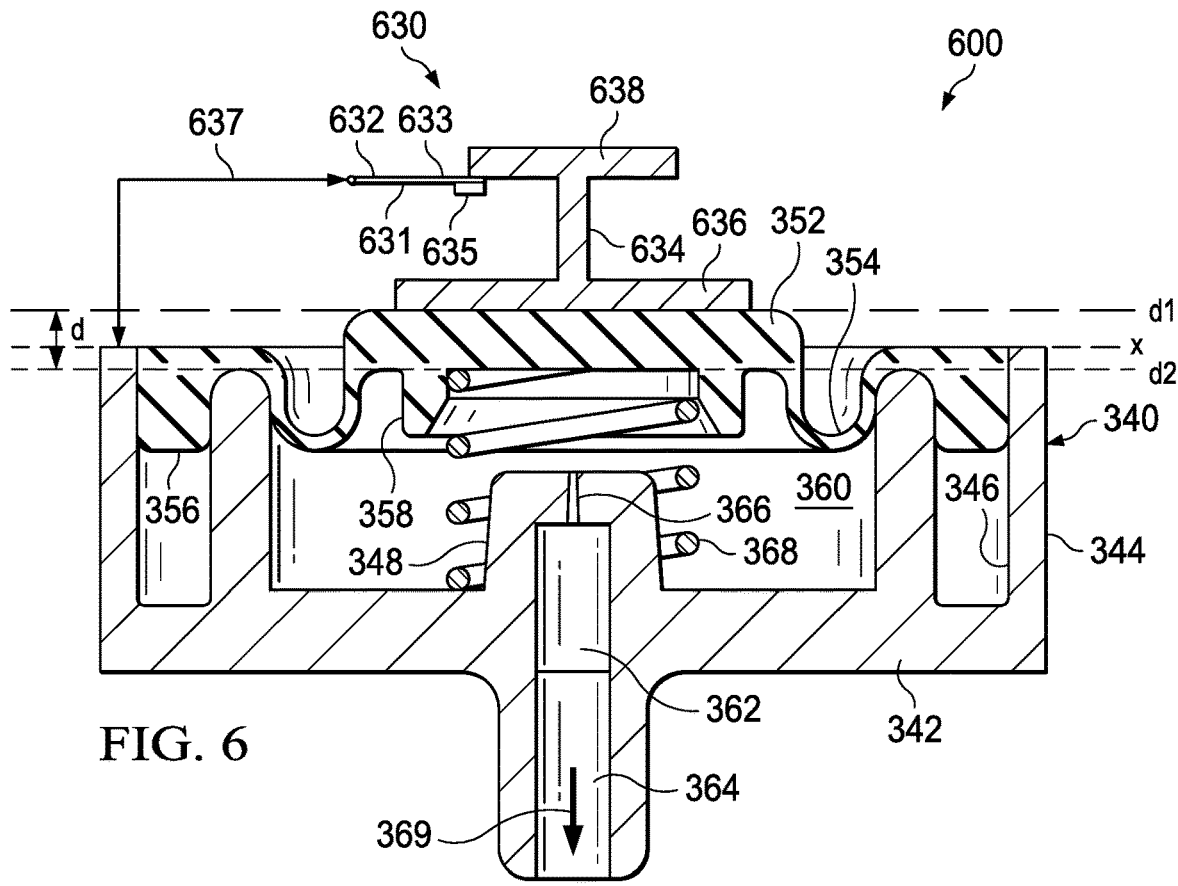
FIG. 6 is a schematic, cross-sectional view of a second embodiment of the pressure switch mechanism of FIG. 3 including the pneumatic actuator and a second example embodiment of a switching element comprising a cantilever-spring, latching electromechanical switch to deliver negative pressure in accordance with this specification.

In another example embodiment, the switching element 330 including the actuator portion 332 and the diaphragm portion 334 may be a cantilever-spring electromechanical switch shown in FIG. 6 as switching element 630 including an actuator portion 632 and a diaphragm portion 634 that function in a substantially similar fashion as described above. The actuator portion 632 may be a cantilever spring having a first end 631 in a fixed position relative to the position of the pneumatic actuator 340 as indicated by bidirectional arrow 637 and the dashed reference line (x), and a second end 633 opposite the first end 631. The second end 633 may have a contact surface on the upper side that provides electrical contact and an insulator node 635 on the lower side that only provides physical contact and is not conductive. The diaphragm portion 634 may include an electrical contact having a cross-sectional shape of an I-beam with two flanges, a first flange 636 of which is mechanically coupled to the diaphragm membrane 352 in a fixed relationship with the position of the diaphragm membrane 352, and a second flange 638 opposite the first flange 636. The second flange 638 provides electrical contact for the diaphragm portion 634 and moves together with the diaphragm membrane 352 between the relaxed position and the fully compressed position as described above.

The second end 633 of the actuator portion 632 may have a neutral position when not being flexed, such that the second end 633 is positioned below the second flange 638 when the diaphragm portion 634 is in the relaxed position (d1) and above the second flange 638 when the diaphragm portion 634 is in the fully compressed position (d2). The second end 633 of the actuator portion 632 may have biased positions when the second end 633 is pulled downwardly by the lower surface of the second flange 638 as the diaphragm portion 634 moves from the relaxed position (d1) toward the fully compressed position (d2) as shown in FIG. 6B. The actuator portion 632 may have a length sized so that the second end 633 slips off the lower surface of the second flange 638 when the diaphragm portion 634 reaches the fully compressed position (d2) and snaps back like a cantilever spring into the neutral position described above. The actuator portion 632 provides at least one switching signal (S) when the second end 633 of the actuator portion 632 reaches the relaxed position, e.g., a first switching signal (S1), and at least one switching signal (S) when the second end 633 reaches the fully compressed position, e.g., a second switching signal (S2). As indicated above, travel between these two positions provides an indication of the displacement (d) of the coil spring 368 and/or the diaphragm 350 as a result of negative pressure being applied to the dressing 102 or leaking from the dressing 102.

Figure 6A:
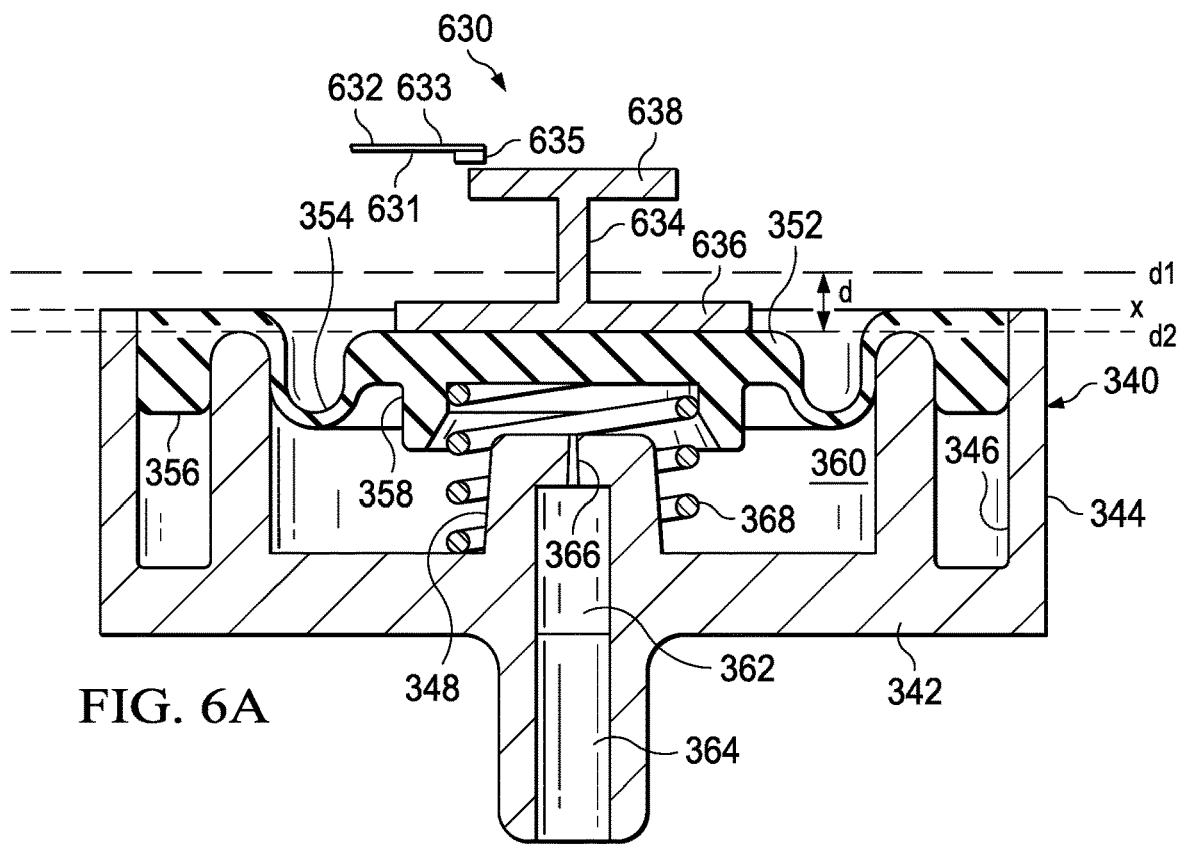
FIGS. 6A-6C are schematic, cross-sectional views of the pneumatic actuator of the pressure switch mechanism of FIG. 6 in a compressed state, a neutral state, and a relaxed state, respectively.
Figure 6B:
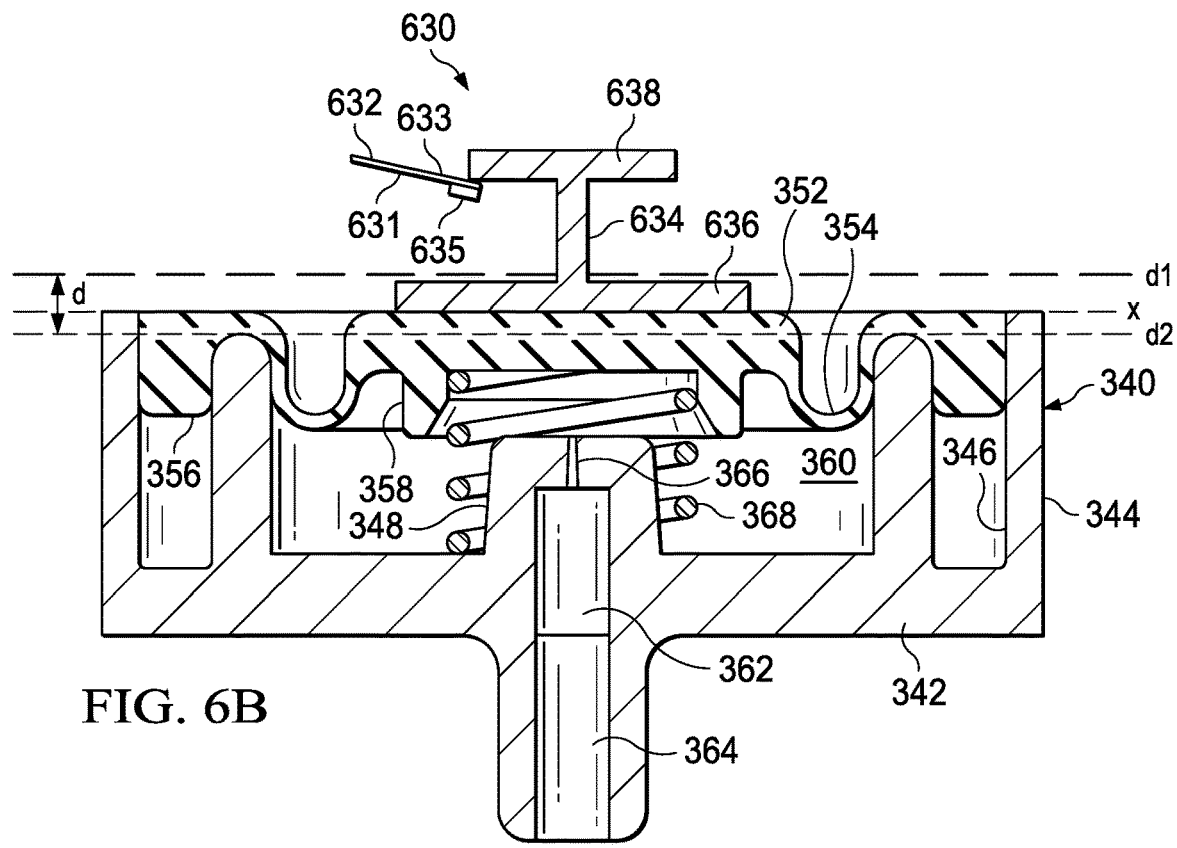
Figure 6C:
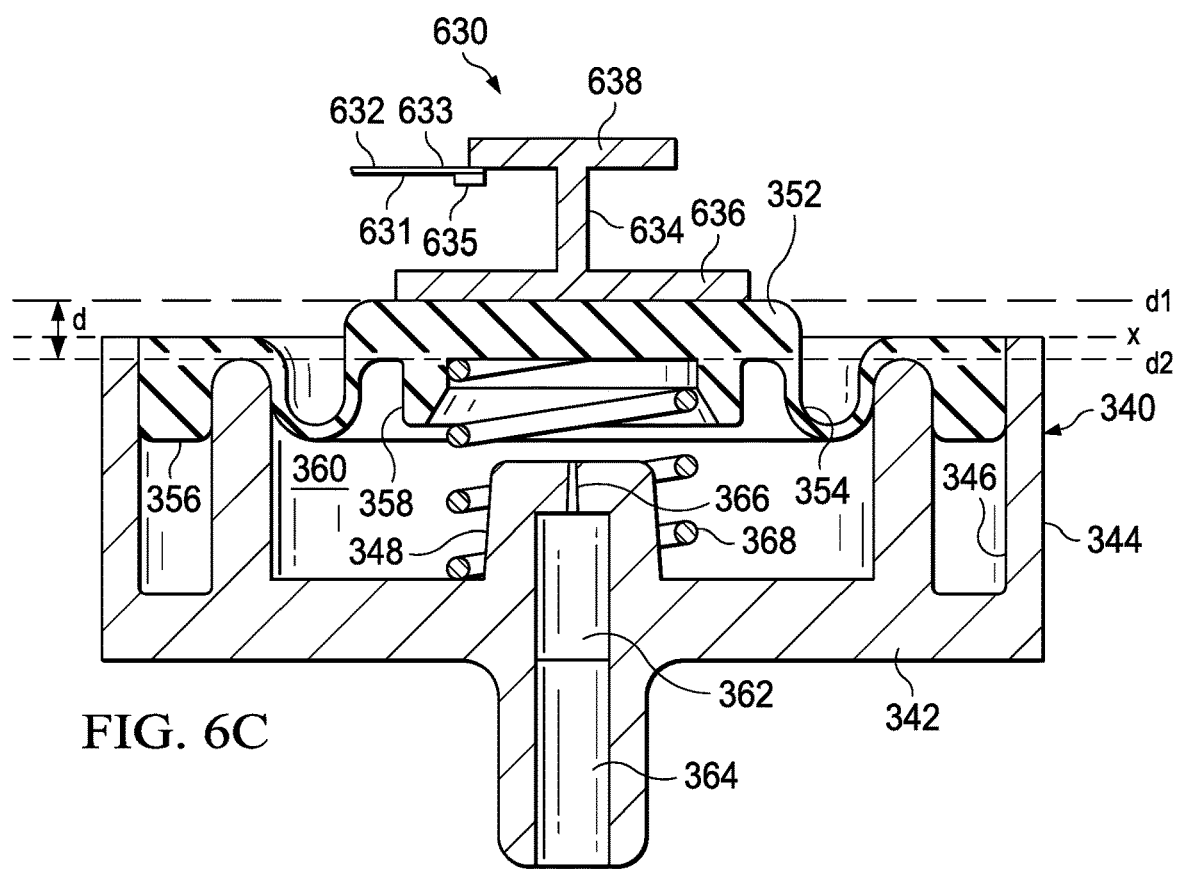

Referring now to FIGS. 6 and 6A-6C, the diaphragm portion 634 of the switching element 630 moves between a relaxed position (d1) and a fully compressed position (d2) as shown in FIGS. 6C and 6A, respectively, with respect to a fixed position of the actuator portion 632 as indicated by bidirectional arrow 637 in FIG. 6 and a dashed reference line (x) in FIGS. 6A-6C. The diaphragm portion 634 moves between the relaxed position (d1) and the fully compressed position (d2) through a biased range of positions corresponding to the neutral state of the coil spring 368 as shown in FIG. 6B. More specifically, the diaphragm portion 634 of the switching element 630 may be displaced from the relaxed position (d1) as shown in FIG. 6C, corresponding to a relaxed state of the coil spring 368, toward the fully compressed position (d2) as shown in FIG. 6A, corresponding to a compressed state of the coil spring 368. Thus, the diaphragm portion 634 increases the displacement (d) while moving through the biased range of positions as shown in FIG. 6B when the coil spring 368 compresses. As the second flange 638 continues moving toward the fully compressed position (d2), it continues pulling down the second end 633, which continues to bend or flex through the biased range of positions. When the diaphragm portion 634 reaches the fully compressed position (d2), the second end 633 of the actuator portion 632 has sufficient flexibility to slip off the lower side of the second flange 638 of the diaphragm portion 634 and snap back up to the neutral position above the second flange 638 so that the contact surface of the second end 633 breaks electrical contact with the second flange 638 of the diaphragm portion 634 as shown in FIG. 6A. This displacement occurs when negative pressure is applied to the dressing 102 and the tissue site 150 as describe above. The second end 633 may be constructed of any material or composite material having sufficient flexibility to slip off the lower side of the second flange 638. Moreover, the material forming the second end 633 may be selected to reduce the flexibility of the second end 633 so that it supplements the opposing force of the coil spring 368 to provide additional hysteresis when applying negative pressure to the dressing 102 and the tissue site 150.

When negative pressure leaks from the dressing 102 and the tissue site 150 and the switch pressure (SP) reaches the minimum target pressure (TPmin) as a result of the leaks as describe above, the diaphragm portion 634 begins moving toward the relaxed position (d1). The diaphragm portion 634 of the switching element 630 is displaced in the opposite direction, or upwardly, from the fully compressed position (d2) as shown in FIG. 6A, corresponding to a compressed state of the coil spring 368, toward the relaxed position (d1) as shown in FIGS. 6 and 6C, corresponding to a relaxed state of the coil spring 368. Thus, the diaphragm portion 634 decreases displacement (d) while moving through the biased range of positions as shown in FIG. 6B when the coil spring 368 decompresses. The second flange 638 continues moving toward the second end 633 until it reaches the insulator node 635. When the upper surface of the second flange 638 contacts the insulator node 635 that prevents electrical contact, the second flange 638 continues moving and pushes the second end 633 upwardly until the second end 633 snaps back to the neutral position below the second flange 638 so that the contact surface of the second end 633 makes electrical contact with the lower side of the second flange 638 where the second flange 638 is in the relaxed position (d1) as shown in FIGS. 6 and 6C.

The switching element 630 may provide the switching signal (S) alternately at the relaxed position (d1) when the coil spring 368 is in the relaxed state to provide a first switching signal (S1) and at the fully compressed position (d2) when the coil spring 368 is in the compressed state to provide a second switching signal (S2), but no switching signal (S) in the neutral state as represented by the biased positions. When the diaphragm portion 634 reaches the fully compressed position (d2) as described above, the electrical contact surface of the second end 633 breaks electrical contact with the second flange 638 of the diaphragm portion 634 to provide the second switching signal (S2). Correspondingly, when the diaphragm portion 634 reaches the relaxed position (d1) as described above, the second end 633 snaps back so that the electrical contact surface of the second end 633 makes electrical contact with the lower side of the second flange 638 as shown in FIG. 6C to provide the first switching signal (S1). The switching element 630 also may include a switching module substantially similar to the switching module 336 described above that turns the negative-pressure source 304 on and off via the controller 310 in response to the switching signal (S) that toggles between the first switching signal (S1), e.g., an open-circuit signal, and the second switching signal (S2), e.g., a closed-circuit signal. The switching element 630 may provide the switching signals (S) to the switching module 336 fashion similar to that set forth in Table II.

TABLE II

| State of System | Diaphram Position | Switching Element | Switching Signals(s) |
|---|---|---|---|
| Start evacuation | Relaxed | Close | 0-1 |
| Evacuating | Neutral | Stays closed | 1 |
| Pump off (Tmax) | Compressed | Opens | S2:1-0 |
| Steady State | Neutral | Stays open | 0 |
| Pump on (Tmin) | Relaxed | Closes | S1:0-1 |
| Evacuating | Neutral | Stays closed | 1 |

Figure 7:
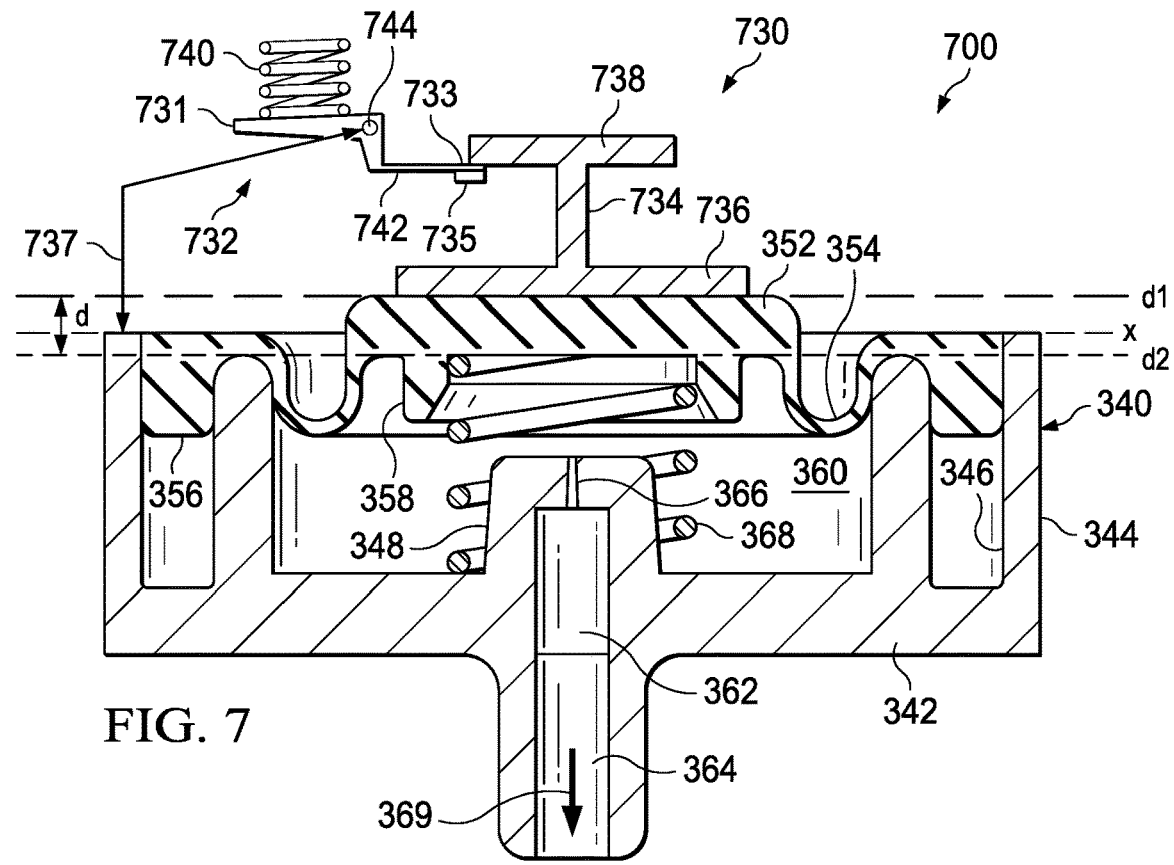
FIG. 7 is a schematic, cross-sectional view of a third embodiment of the pressure switch mechanism of FIG. 3 including the pneumatic actuator and a third example embodiment of a switching element comprising a opposing-spring, latching electromechanical switch to deliver negative pressure in accordance with this specification.

In another example embodiment, the switching element 330 including the actuator portion 332 and the diaphragm portion 334 may be an opposing-spring electromechanical switch shown as switching element 730 in FIG. 7 including an actuator portion 732 and a diaphragm portion 734 that function in a substantially similar fashion as described above. The actuator portion 732 may include a latching spring 740 that may be a compression type coil spring and a lever 742 rotationally mounted on a pin 744 having a fixed position relative to the position of the pneumatic actuator 340 as indicated by bidirectional arrow 737 and at the dashed reference line (x). The lever 742 may include two ends, a first end 731 mechanically coupled to one end of the latching spring 740 and a second end 733 opposite the first end 731. The second end 733 may have a contact surface on the upper side that provides electrical contact and an insulator node 735 on the lower side that only provides physical contact as an insulator. The diaphragm portion 734 may include an electrical contact having a cross-sectional shape of an I-beam with two flanges, a first flange 736 of which is mechanically coupled to the diaphragm membrane 352 in a fixed relationship with the position of the diaphragm membrane 352, and a second flange 738 opposite the first flange 736. The second flange 738 provides electrical contact for the diaphragm portion 734 and moves together with the diaphragm membrane 352 between the relaxed position and the fully compressed position as described above.

The second end 733 of the lever 742 may have a neutral position when the latching spring 740 is in a relaxed state, such that the second end 733 is positioned below the second flange 738 when the diaphragm portion 734 is in the relaxed position (d1), and above the second flange 738 when the lever 742 is in the fully compressed position (d2). The second end 733 of the lever 742 may have biased positions when the second end 733 is pulled downwardly by the lower surface of the second flange 738 as the diaphragm portion 734 moves from the relaxed position (d1) toward the fully compressed position (d2) compressing the latching spring 740 from its relaxed state as shown in FIG. 7B. The lever 742 may have a length sized so that the second end 733 slips off the lower surface of the second flange 738 when the diaphragm portion 734 reaches the fully compressed position (d2) and snaps back into the neutral position described above. The actuator portion 732 provides at least one switching signal (S) when the second end 733 of the lever 742 reaches the relaxed position, e.g., a first switching signal (S1), and at least one switching signal (S) when the second end 733 reaches the fully compressed position, e.g., a second switching signal (S2). As indicated above, travel between these two positions provides an indication of the displacement (d) of the coil spring 368 and/or the diaphragm 350 as a result of negative pressure being applied to the dressing 102 or leaking from the dressing 102.

Figure 7A:
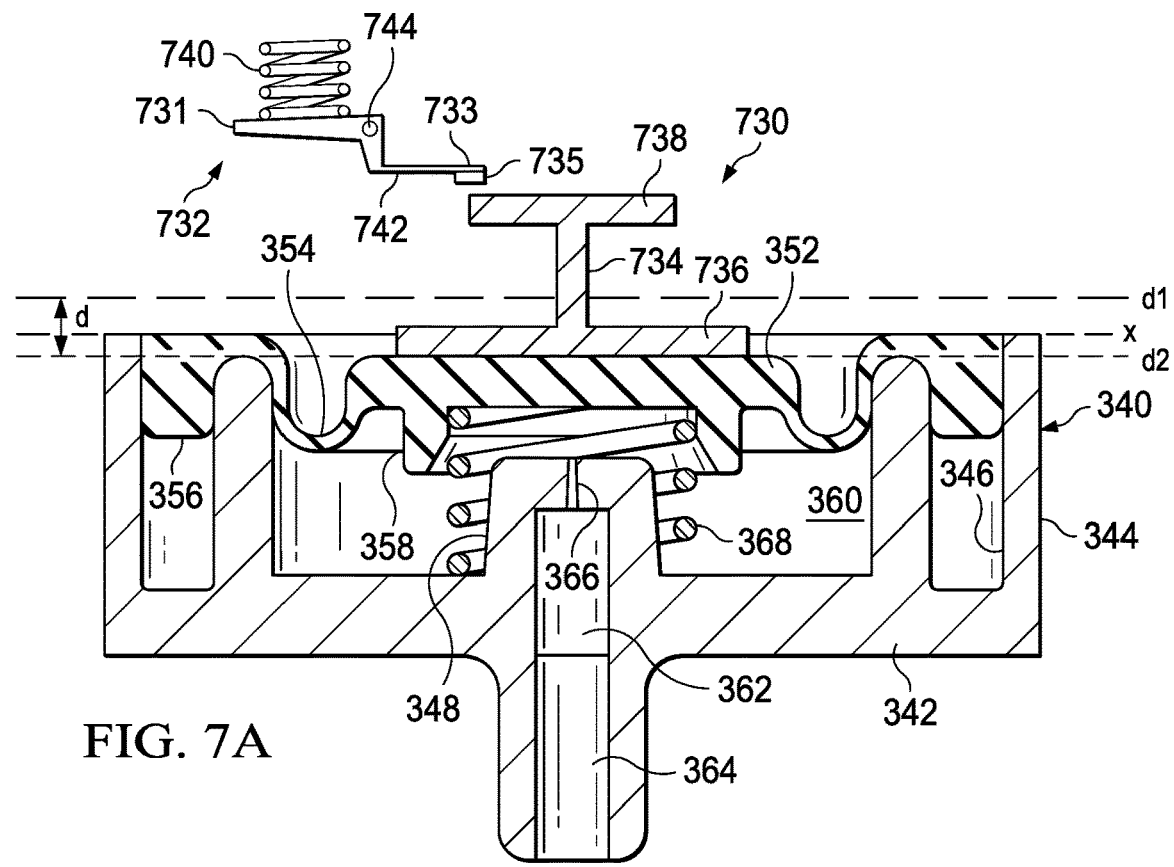
FIGS. 7A-7C are schematic, cross-sectional views of the pneumatic actuator of the pressure switch mechanism of FIG. 7 in a compressed state, a neutral state, and a relaxed state, respectively.
Figure 7B:
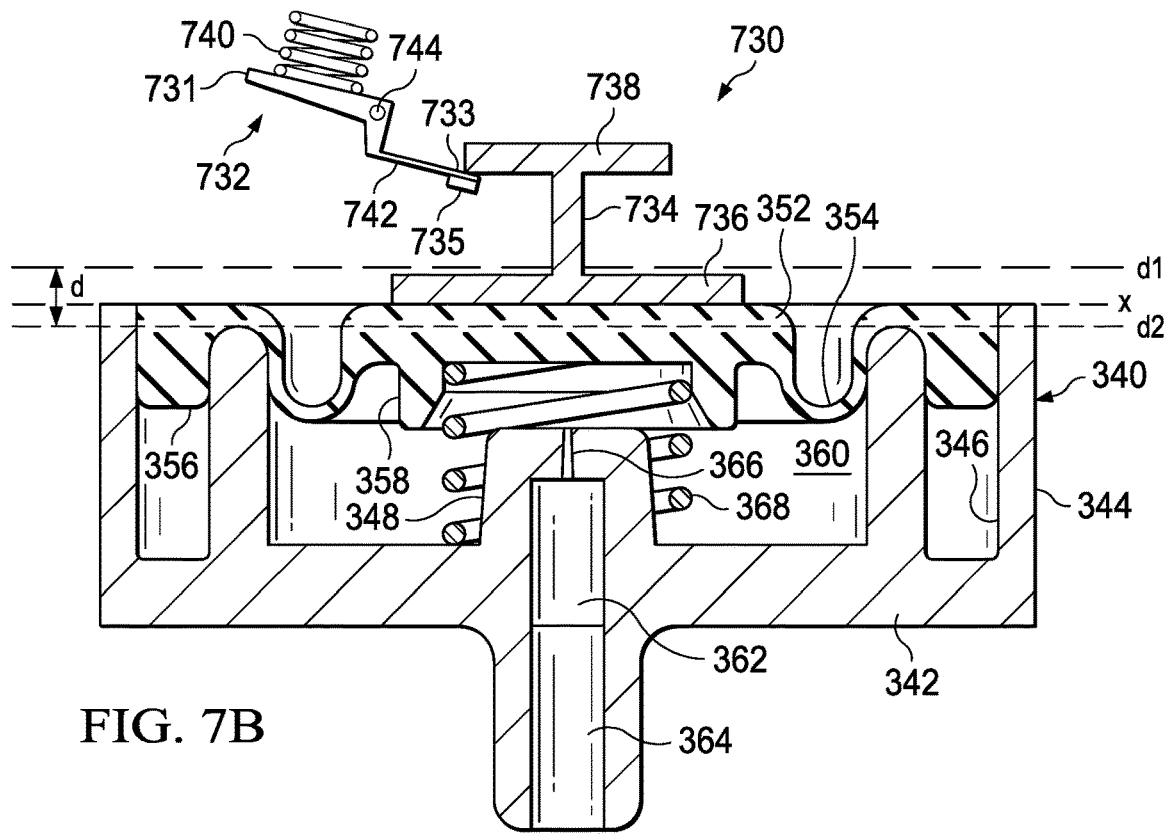
Figure 7C:
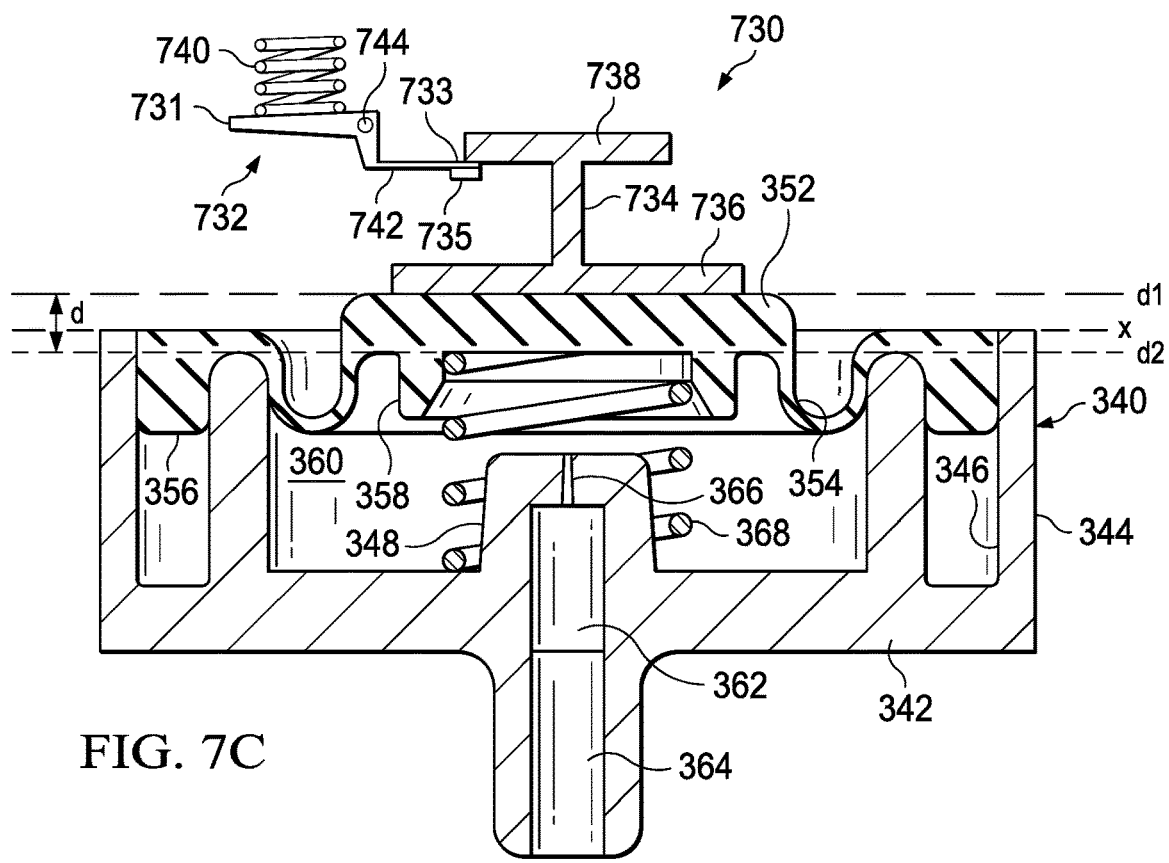

Referring now to FIGS. 7 and 7A-7C, the diaphragm portion 734 of the switching element 730 moves between a relaxed position (d1) and a fully compressed position (d2) as shown in FIGS. 7C and 7A, respectively, with respect to a fixed position of the actuator portion 332 as indicated by bidirectional arrow 737 in FIG. 7 and a dashed reference line (x) in FIGS. 7A-7C. The diaphragm portion 734 moves between the relaxed position (d1) and the fully compressed position (d2) through a biased range of positions corresponding to the neutral state of the coil spring 368 as shown in FIG. 7B. More specifically, the diaphragm portion 734 of the switching element 730 may be displaced from the relaxed position (d1) as shown in FIG. 7C, corresponding to a relaxed state of the coil spring 368, toward the fully compressed position (d2) as shown in FIG. 7A, corresponding to a compressed state of the coil spring 368. Thus, the diaphragm portion 734 increases the displacement (d) while moving through the biased range of positions as shown in FIG. 7B when the coil spring 368 compresses. As the second flange 738 continues moving toward the fully compressed position (d2), it continues pulling down the second end 733, as the latching spring 740 continues to compress through the biased range of positions. When the diaphragm portion 734 reaches the fully compressed position (d2), the second end 733 reaches a position allowing it to slip off the lower side of the second flange 738 of the diaphragm portion 634 so that the fully compressed latching spring 740 causes the second end 733 to snap back up to the neutral position above the second flange 638. As a result, the contact surface of the second end 733 breaks electrical contact with the second flange 738 of the diaphragm portion 734 as shown in FIG. 7A. This displacement occurs when negative pressure is applied to the dressing 102 and the tissue site 150 as describe above. The latching spring 740 may have spring constant of sufficient magnitude to ensure that the second end 733 snaps back to the neutral position when it slips off the lower side of the second flange 738. Moreover, the spring constant of the latching spring 740 may be selected to supplement the opposing force of the coil spring 368 order to provide additional hysteresis when applying negative pressure to the dressing 102 to the tissue site 150.

When negative pressure leaks from the dressing 102 and the tissue site 150 and the switch pressure (SP) reaches the minimum target pressure (TPmin) as a result of the leaks as describe above, the diaphragm portion 734 begins moving toward the relaxed position (d1). The diaphragm portion 734 of the switching element 730 is displaced in the opposite direction, or upwardly, from the fully compressed position (d2) as shown in FIG. 7A, corresponding to a compressed state of the coil spring 368, toward the relaxed position (d1) as shown in FIGS. 7 and 7C, corresponding to a relaxed state of the coil spring 368. Thus, the diaphragm portion 734 decreases displacement (d) while moving through the biased range of positions as shown in FIG. 7B when the coil spring 368 decompresses. The second flange 738 continues moving toward the second end 733 until it reaches the insulator node 735. When the upper surface of the second flange 738 contacts the insulator node 735 that prevents electrical contact, the second flange 738 continues moving and pushes the second end 733 upwardly until the second end 733 snaps back to the neutral position below the second flange 738 so that the contact surface of the second end 733 makes electrical contact with the lower side of the second flange 738 where the second flange 738 is in the relaxed position (d1) as shown in FIGS. 7 and 7C.

The switching element 730 may provide the switching signal (S) alternately at the relaxed position (d1) when the coil spring 368 is in the relaxed state to provide a first switching signal (S1) and at the fully compressed position (d2) when the coil spring 368 is in the compressed state to provide a second switching signal (S2), but no switching signal (S) in the neutral state as represented by the biased positions. When the diaphragm portion 734 reaches the fully compressed position (d2) as described above, the electrical contact surface of the second end 733 breaks electrical contact with the second flange 738 of the diaphragm portion 734 to provide the second switching signal (S2). Correspondingly, when the diaphragm portion 734 reaches the relaxed position (d1) as described above, the second end 733 snaps back so that the electrical contact surface of the second end 733 makes electrical contact with the lower side of the second flange 738 as shown in FIG. 7C to provide the first switching signal (S1). The switching element 730 also may include a switching module substantially similar to the switching module 336 described above that turns the negative-pressure source 304 on and off via the controller 310 in response to the switching signal (S) that toggles between the first switching signal (S1), e.g., an open-circuit signal, and the second switching signal (S2), e.g., a closed-circuit signal. The switching element 730 may provide the switching signals (S) to the switching module 336 fashion similar to that set forth in Table 2 above.

Figure 8:
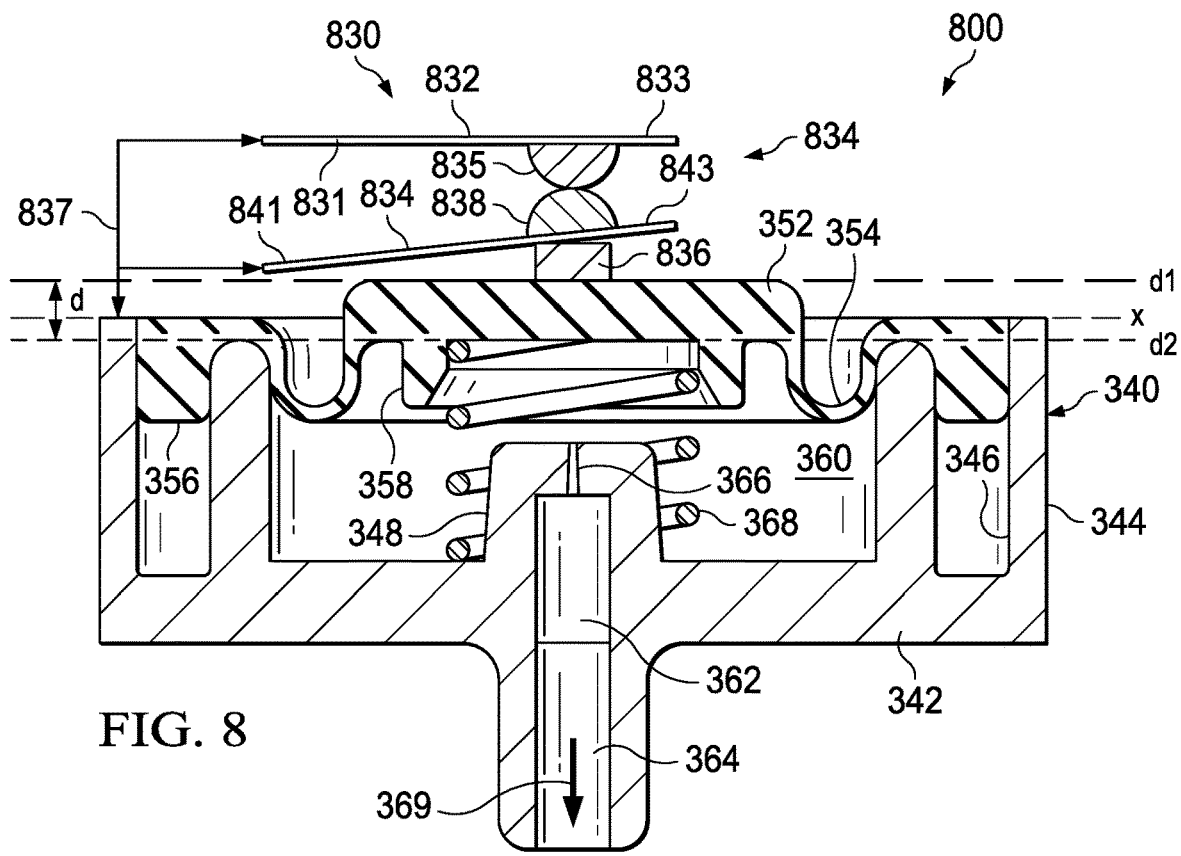
FIG. 8 is a schematic, cross-sectional view of a fourth embodiment of the pressure switch mechanism of FIG. 3 including the pneumatic actuator and a fourth example embodiment of a switching element comprising a magnetic electromechanical switch to deliver negative pressure in accordance with this specification.

In another example embodiment, the switching element 330 including the actuator portion 332 and the diaphragm portion 334 may be a magnetic electromechanical switch shown as switching element 830 in FIG. 8 including an actuator portion 832 and a diaphragm portion 834 that function in a substantially similar fashion as described above. The actuator portion 832 may be a cantilever spring having a first end 831 in a fixed position relative to the position of the pneumatic actuator 340 as indicated by bidirectional arrow 837 and the dashed reference line (x), and a second end 833 opposite the first end 831 having a ferrous contact 835 on the lower side that is electrically conductive. The diaphragm portion 834 also may be a cantilever spring having a first end 841 in a fixed position relative to the position of the pneumatic actuator 340 as indicated by bidirectional arrow 837 and the dashed reference line (x), and a second end 843 opposite the first end 841 having a magnetic contact 838 on the upper side that is also electrically conductive. The second end 843 is mechanically coupled to the diaphragm membrane 352 in a fixed relationship with the position of the diaphragm membrane 352 by a joint member 836. The magnetic contact 838 provides electrical contact with the ferrous contact 835 and moves together with the diaphragm membrane 352 between the relaxed position and the fully compressed position as described above.

Figure 8A:
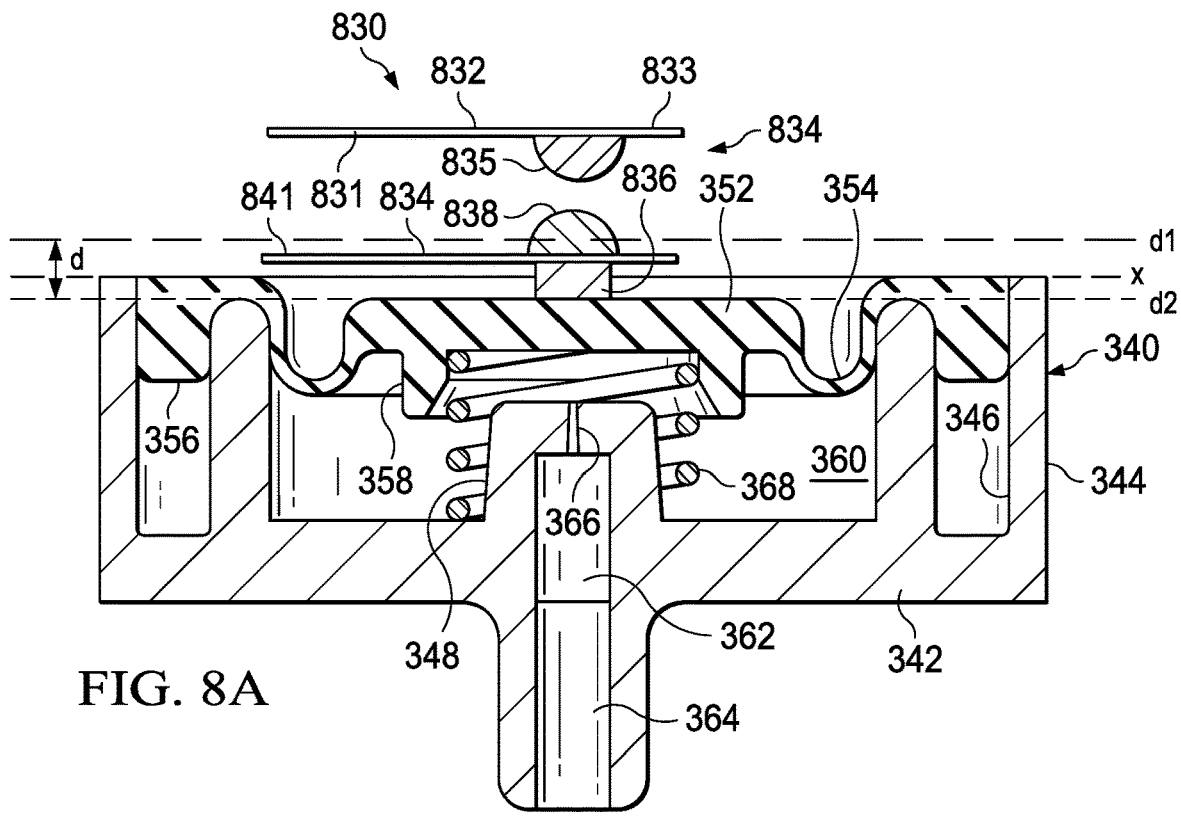
FIGS. 8A-8C are schematic, cross-sectional views of the pneumatic actuator of the pressure switch mechanism of FIG. 8 in a compressed state, a neutral state, and a relaxed state, respectively.
Figure 8B:
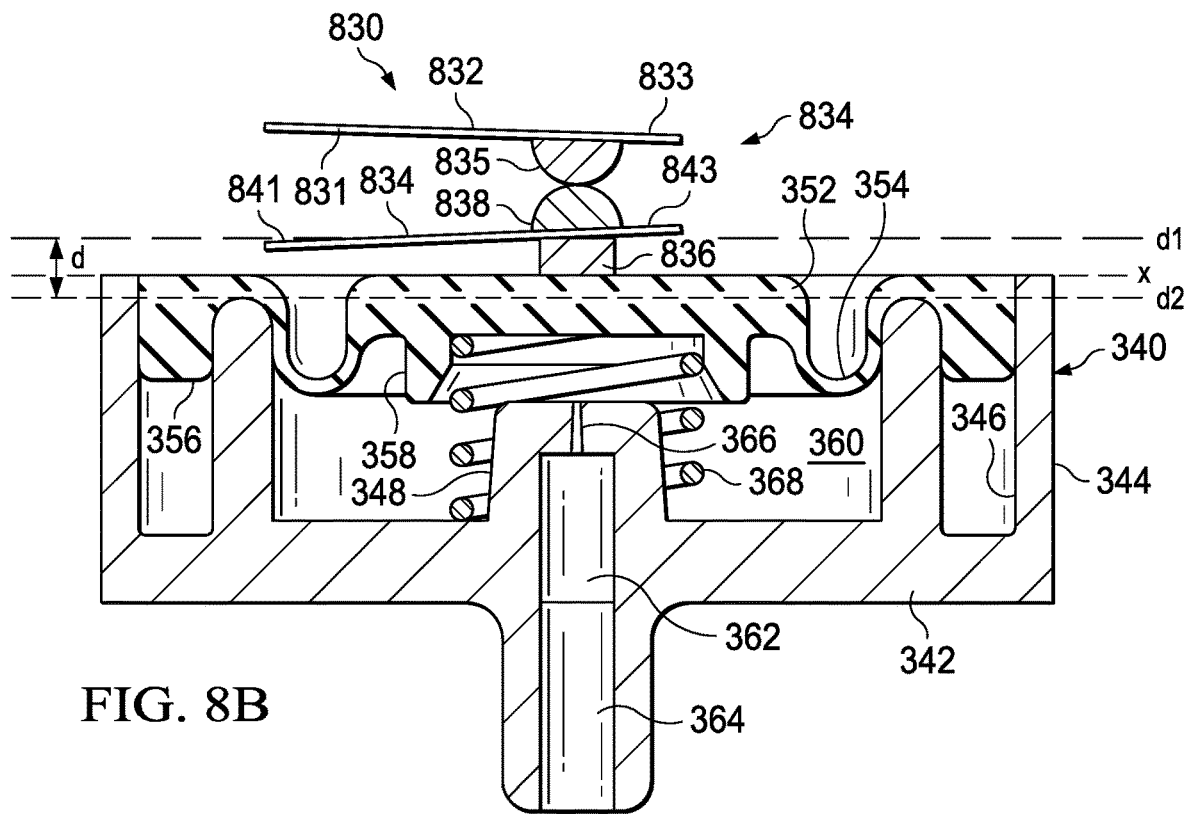
Figure 8C:
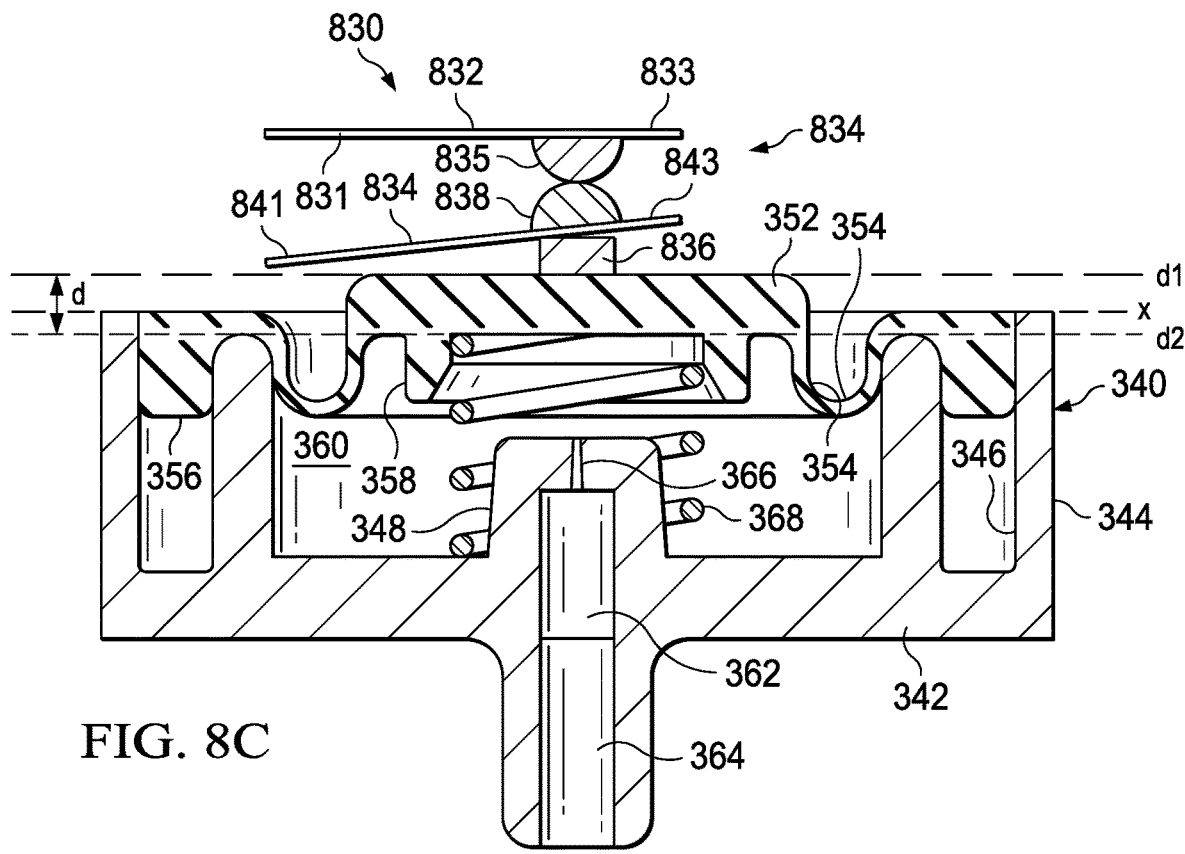

Referring now to FIGS. 8 and 8A-8C, the diaphragm portion 834 of the switching element 830 moves between a relaxed position (d1) and a fully compressed position (d2) as shown in FIGS. 8C and 8A, respectively, with respect to a fixed position of the actuator portion 832 as indicated by bidirectional arrow 837 in FIG. 8 and a dashed reference line (x) in FIGS. 8A-8C. The diaphragm portion 834 moves between the relaxed position (d1) and the fully compressed position (d2) through a biased range of positions corresponding to the neutral state of the coil spring 368 as shown in FIG. 8B. More specifically, the diaphragm portion 834 of the switching element 830 may be displaced from the relaxed position (d1) as shown in FIG. 8C, corresponding to a relaxed state of the coil spring 368, toward the fully compressed position (d2) as shown in FIG. 8A, corresponding to a compressed state of the coil spring 368. Thus, the diaphragm portion 834 increases the displacement (d) while moving through the biased range of positions as shown in FIG. 8B when the coil spring 368 is being compressed. During the neutral state, the magnetic contact 838 engages the ferrous contact 835 to provide an electrical contact or closed circuit. As the magnetic contact 838 continues moving toward the fully compressed position (d2), it continues pulling down the second end 833 of the actuator portion 832, which continues to bend or flex through the biased range of positions. When the diaphragm portion 834 reaches the fully compressed position (d2), the second end 833 of the actuator portion 832 has sufficient stiffness to overcome the magnetic force of the magnetic contact 838 so that it snaps away from the diaphragm portion 834 and causes the ferrous contact 835 breaks electrical contact with the magnetic contact 838 of the diaphragm portion 834 as shown in FIG. 8A. This displacement occurs when negative pressure is applied to the dressing 102 and the tissue site 150 as describe above. The actuator portion 832 may be constructed of any material or composite material having sufficient stiffness to overcome the magnetic force of the magnetic contact 838. Moreover, the material forming the actuator portion 832 may be selected to further reduce the flexibility of the actuator portion 832 so that it supplements the opposing force of the coil spring 368 to provide additional hysteresis when applying negative pressure to the dressing 102 and the tissue site 150.

When negative pressure leaks from the dressing 102 and the tissue site 150 and the switch pressure (SP) reaches the minimum target pressure (TPmin) as a result of the leaks as describe above, the diaphragm portion 834 begins moving toward the relaxed position (d1). The diaphragm portion 834 of the switching element 830 is displaced in the opposite direction, or upwardly, from the fully compressed position (d2) as shown in FIG. 8A, corresponding to a compressed state of the coil spring 368, toward the relaxed position (d1) as shown in FIGS. 8 and 8C, corresponding to a relaxed state of the coil spring 368. Thus, the diaphragm portion 834 decreases displacement (d) while moving through the biased range of positions as shown in FIG. 8B when the coil spring 368 decompresses. The magnetic contact 838 also begins moving back toward the ferrous contact 835 and continues moving upwardly until the actuator portion 832 reaches the relaxed position (d1) as shown in FIGS. 8 and 8C. When the magnetic contact 838 reaches the relaxed position (d1), the magnetic field is close enough to the ferrous contact 835 causing the ferrous contact 835 to snap back into electrical contact with the magnetic contact 838. The actuator portion 832 provides at least one switching signal (S) when the second end 833 of the actuator portion 832 reaches the relaxed position, e.g., a first switching signal (S1), and at least one switching signal (S) when the second end 833 reaches the fully compressed position, e.g., a second switching signal (S2). As indicated above, travel between these two positions provides an indication of the displacement (d) of the coil spring 368 and/or the diaphragm 350 as a result of negative pressure being applied to the dressing 102 or leaking from the dressing 102.

The switching element 830 may provide the switching signal (S) alternately at the relaxed position (d1) when the coil spring 368 is in the relaxed state to provide a first switching signal (S1) and at the fully compressed position (d2) when the coil spring 368 is in the compressed state to provide a second switching signal (S2), but no switching signal (S) in the neutral state as represented by the biased positions. When the diaphragm portion 834 reaches the fully compressed position (d2) as described above, the ferrous contact 835 of the actuator portion 832 breaks electrical contact with the magnetic contact 838 of the diaphragm portion 834 to provide the second switching signal (S2). Correspondingly, when the diaphragm portion 834 reaches the relaxed position (d1) as described above, the ferrous contact 835 comes back within the magnetic field of the magnetic contact 838 causing the second end 833 of the actuator portion 832 to be pulled back toward the diaphragm portion 834 so that the ferrous contact 835 makes electrical contact with the magnetic contact 838 as shown in FIG. 8C to provide the first switching signal (S1). The switching element 830 also may include a switching module substantially similar to the switching module 336 described above that turns the negative-pressure source 304 on and off via the controller 310 in response to the switching signal (S) that toggles between the first switching signal (S1), e.g., a closed-circuit signal, and the second switching signal (S2), e.g., an open-circuit signal. The switching element 830 may provide the switching signals (S) to the switching module 336 fashion similar to that set forth in Table 2.

The switching element 330 may be any electromechanical device that is operatively coupled directly to the negative-pressure source 304 or indirectly via the controller 310, and may also include the switching module 336 as described above. In one example embodiment of the switching module 336, the switching module 336 may be electronic circuitry or software that may be a portion of or stored on the controller 310 or the pressure switch mechanism 300. The switching signals (S) may be any type of signal such as, for a low or high digital signal, depending on the type of switching module 336 being utilized. In one example embodiment, the electronic circuitry may be a T-type flip-flop that changes states between the relaxed state and the compressed state whenever its clock input is strobed by the switching signal (S), which alternates between the first switching signal (S1) that turns on the negative-pressure source 304 in the relaxed state and the second switching signal (S2) the turns off the negative-pressure source 304 and the compressed state, but holds the previous state value during the intermediate neutral state when no switching signal (S) is being provided to the clock input.

Figure 9:
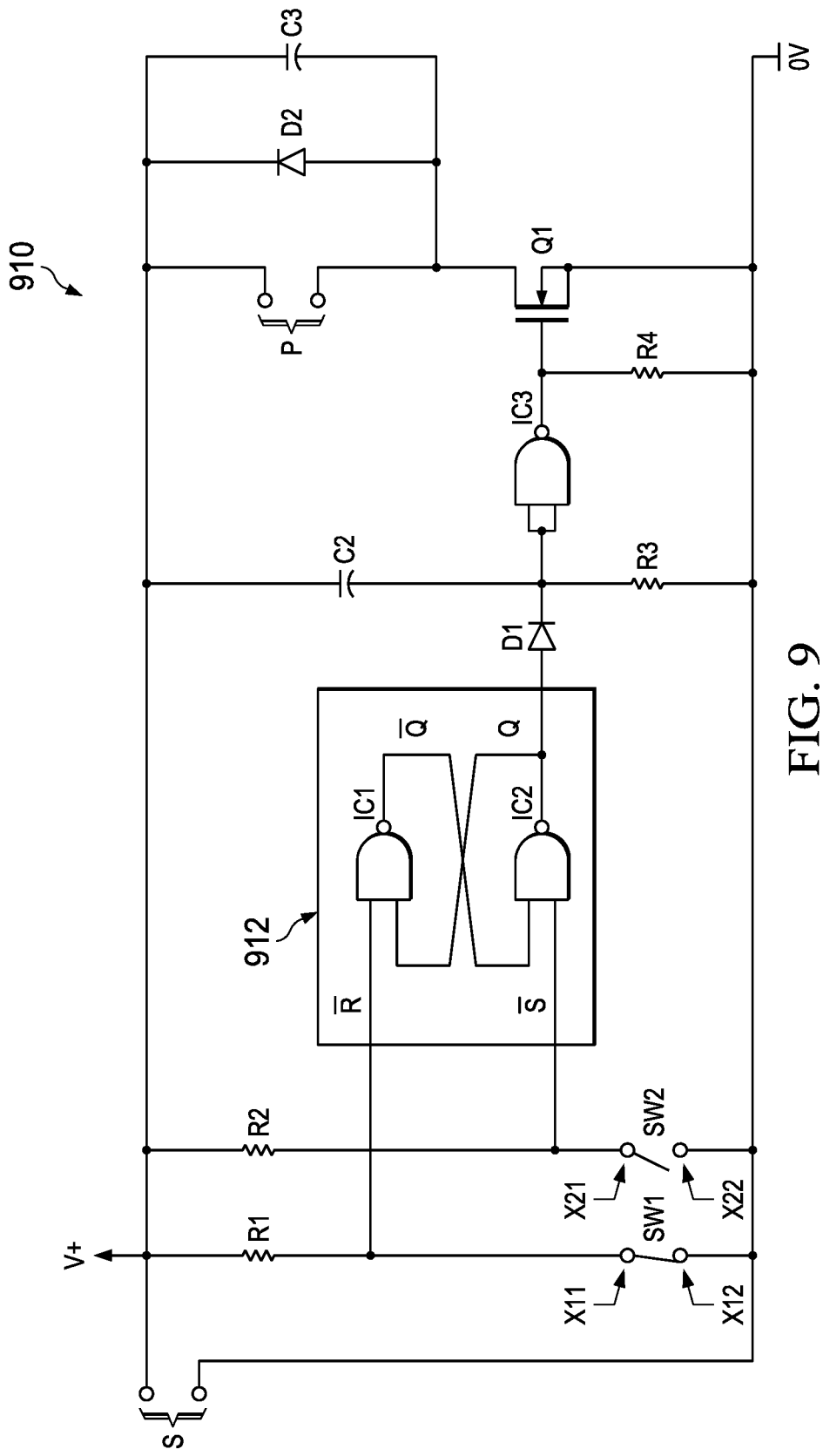
FIG. 9 is an electrical schematic of a flip-flop circuit including an RC network that may be used with the switching elements of FIGS. 3, 5, 6, 7, and 8 in accordance with this specification, and more specifically using a single-pole, double-throw (SPDT) type of pressure switch as a component of the switching element; and, FIG. 10 is an electrical schematic of an RC signal inverting circuit that may be used with the switching elements of FIGS. 3, 5, 6, 7, and 8 in accordance with this specification, and more specifically using a single-pole, single-throw (SPST) pressure switch as a component of the switching element.

In another example embodiment of the switching module 336, the switching module 336 may be a single-pole, double-throw (SPDT) switch shown as switching module 910 in FIG. 9 and embodied in electronic circuitry that may be a portion of or stored on the controller 310 or the pressure switch mechanism 300. The switching module 910 may be used with any one of the switching elements 330, 530, 630, 730, and 830 to turn the negative-pressure source 304 on and off as described in detail above. The switching module 910 may include an SR latch type flip-flop such as, for example, SR NAND latch flip-flop shown as flip-flop 912 including two NAND gates IC1 and IC2 connected in a cross-NAND set-reset arrangement. Respective inputs of the NAND gates IC1 and IC2 communicate with switches SW1 and SW2, a normally closed switch and a normally open switch respectively, which are responsive to actuation of the switching module 336. The flip-flop 912 provides an output to toggle a pump signal (P) to selectively turn the pump of the negative-pressure source 304 on and off according to the switching signal (S) described above and states of the switches SW1 and SW2 as described below.

The switches SW1 and SW2 each have two terminals, i.e., terminals X11 and X12 for switch SW1 and terminals X21 and X22 for switch SW2. For the switching module 336 to implement change-over contacts or two separate contacts, a normally-closed contact of the switching module 336 is connected to the terminal X11 of the switch SW1 that is connected to V+ through resistor R1. Conversely, a normally-open contact of the switching module 336 is connected to the terminal X21 of the switch SW2 that is connected to V− through resistor R2. A common contact of the switching module 336 is connected to the terminals X12 and X22 of the switch SW1 and the switch SW2, respectively, that are connected to 0V as shown in FIG. 9.

When the switching module 336 is initially powered on, the switch SW1 is closed, connecting the input of IC1 to 0V (i.e., 0 or low) and causing IC1 to output 1 (i.e., high). At the same time, the switch SW2 so that the input of IC2 to be pulled up to V+(i.e., 1 or high), causing IC2 to output 0 (i.e., low) and the Q output of the flip-flop 312 to also go low. An RC network comprising capacitor C2 and resistor R3 begins to charge the capacitor C2 through the resistor R3. After a duration of approximately R×C seconds (where R is a resistance of R3 and C is a capacitance of C2), inverter IC3 switches (e.g., from an output of 0 to an output of 1) to turn on transistor (e.g., a MOSFET) Q1, causing the pump signal (P) to toggle on. In other words, the RC network provides a delay after an initial power up of the switching module 336 prior to turning on the pump of the negative-pressure source 304. For example only, if R is 1 MΩ and the C is 0.47 µF, then the delay may be approximately 0.5 seconds.

When the maximum target pressure (TP max) is reached, the switching module 336 actuates as described above in FIGS. 1-8, causing the switch SW1 that is normally closed to open and the switch SW2 that is normally open to close. Accordingly, the input of IC1 is pulled high, and the output of IC1 is low. At the same time, the input of IC2 is pulled low to 0V, causing the output of IC2 and the Q output of the flip-flop 312 to be pulled high. The toggling of the output of the flip-flop 312 (e.g., from low to high) causes the capacitor C2 to discharge through diode D1 and IC2, which turns off the transistor Q1 so that the pump signal (P) is toggled off to turn off the pump of the negative-pressure source 304. Accordingly, as described above, if the switching module 336 implements change-over contacts or two separate contacts, the flip-flop 312 and RC network can be used to provide debouncing and a delay to implement a hysteresis band operating below and up to the maximum target pressure (TP max).

Figure 10:
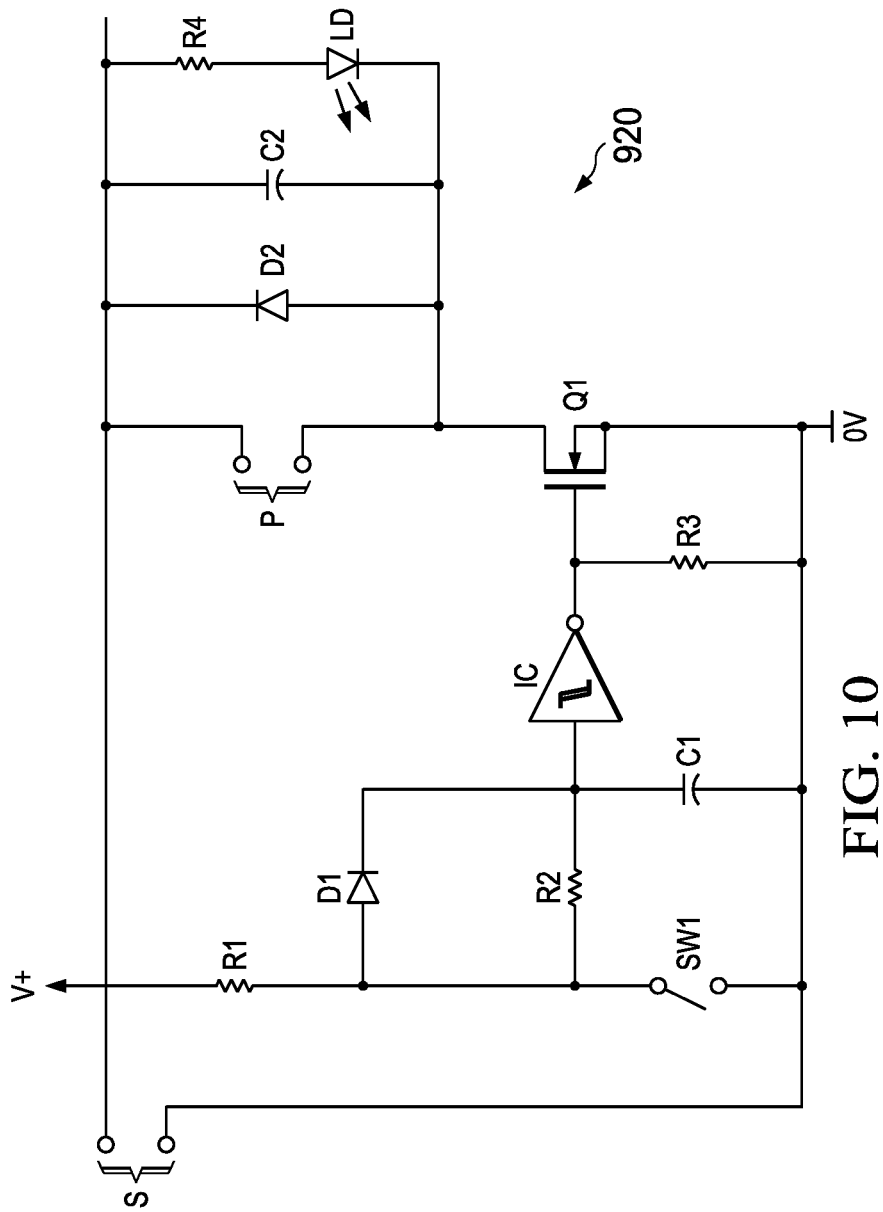

In another example embodiment of the switching module 336, the switching module 336 may be a single-pole, single-throw (SPST) switch shown as switching module 920 in FIG. 10 and embodied in electronic circuitry that may be a portion of or stored on the controller 310 or the pressure switch mechanism 300. The switching module 920 may be used with any one of the switching elements 330, 530, 630, 730, and 830 to turn the negative-pressure source 304 on and off as described in detail above. The switching module 920 may include an inverter gate IC having an input that communicates with switch SW1, which is responsive to actuation of the switching element 330. The inverter gate IC provides an output to toggle pump signal (P), and selectively turn the pump of the negative-pressure source 304 on and off, according to the switching signal (S) and the state of the switch SW1 as described below.

For the switching element 330 to implement a single, normally-closed contact, the pressure switch mechanism 300 is connected to both terminals of switch SW1. When the switching module 336 is initially powered on, the switch SW1 is closed so that the node between resistors R1 and R2, diode D1, and the switch SW1 is connected to 0V, which pulls the input of the inverter gate IC to 0V (i.e., 0, or low) causing the inverter gate IC to output 1 (i.e., high). Accordingly, transistor (e.g., MOSFET) Q1 is turned on, causing the pump signal (P) to toggle on to turn on the pump of the negative-pressure source 304. In other words, if the wound pressure (WP) is lower than the maximum target pressure (TP max), the pump of the negative-pressure source 304 is immediately turned on when the switching module 336 is initially powered on. When the target pressure (TP) is reached, the switching element 330 actuates as described above, causing the switch SW1 to open and capacitor C1 to charge through the resistor R1 and the diode D1. As a result, the input of the inverter gate IC is pulled high to V+ through the resistor R1, causing the inverter gate IC to output 0 (i.e., low). Accordingly, the transistor Q1 is turned off, causing the pump signal (P) to toggle off to turn off the pump of the negative-pressure source 304.

When the wound pressure (WP) falls below the minimum target pressure (TP min), the switch SW1 is closed and the capacitor C1 discharges through the resistor R2 over a duration of approximately R×C seconds (where R is a resistance of R2 and C is a capacitance of C1). When a voltage across the capacitor C1 decreases (due to discharging) below a transition threshold of the input of the inverter gate IC, the output of the inverter gate IC switches high to turn on the transistor Q1 and the pump of the negative-pressure source 304. In other words, when the switch SW1 is closed, the RC network including the capacitor C1 and the resistor R2 delays the pump from being immediately turned on. For example only, if R is 1 MΩ and the C is 1 µF, then the delay may be approximately 1 second. In this manner, the inverter gate IC and the RC network can be used to provide debouncing and a delay to implement a hysteresis band at the target negative pressure.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for applying negative pressure to a tissue site, comprising:
    a dressing including a tissue interface adapted to contact the tissue site and a cover adapted to provide a fluid seal between a therapeutic environment including the tissue interface proximate one side of the cover and a local external environment on the other side of the cover;
    a negative-pressure source fluidly coupled to the dressing and adapted to provide negative pressure to the therapeutic environment;
    a pneumatic actuator having a body closed by a diaphragm forming a vacuum chamber with the body, an inlet coupled to the dressing and forming a passage through the body to fluidly couple the vacuum chamber and the therapeutic environment, the diaphragm adapted to move between a relaxed position and a compressed position in response to pressure in the vacuum chamber generated by the negative pressure;
    a valve disposed in the passage and configured to restrict the flow of gas through the passage; and
    a switching element operatively coupled to the diaphragm and adapted to turn on the negative-pressure source when the diaphragm is in the relaxed position and turn off the negative-pressure source when the diaphragm is in the compressed position.

2. The system of claim 1, further comprising a coil spring having a first end coupled to the diaphragm and a second end coupled to the body of the actuator.

3. The system of claim 2, wherein the diaphragm and the first end of the coil spring move between the relaxed position and the compressed position.

4. The system of claim 1, wherein the body of the pneumatic actuator comprises a base and sidewalls extending from the base to an open end, and wherein the diaphragm closes the open end of the sidewalls.

5. The system of claim 4, wherein the diaphragm comprises a center portion and a peripheral portion extending radially outwardly from the center portion to the open end of the sidewalls.

6. The system of claim 5, wherein the center portion is a membrane and the peripheral portion comprises a flexible skirt.

7. The system of claim 5, further comprising an elastic element having a first end coupled to the center portion of the diaphragm and a second end coupled to the base.

8. The system of claim 7, wherein the elastic element is a coil spring.

9. The system of claim 1, wherein the tissue interface is a manifold.

10. The system of claim 1, further comprising a processor operatively coupled to the negative-pressure source to provide a target pressure to the therapeutic environment in a pressure control mode.

11. The system of claim 10, wherein the pressure control mode is a continuous pressure mode.

12. The system of claim 10, wherein the pressure control mode is an intermittent pressure mode.

13. The system of claim 1, further comprising a processor operatively coupled to the negative-pressure source to provide a variable target pressure to the therapeutic environment in a dynamic pressure mode.

14. The system of claim 1, further comprising a positive-pressure source fluidly coupled to the dressing for delivering a solution to the therapeutic environment and the tissue interface for a predetermined time.

15. The system of claim 14, further comprising a processor operatively coupled to the positive-pressure source to provide the solution to the therapeutic environment in a predetermined dosage.

16. The system of claim 14, further comprising a processor operatively coupled to the positive-pressure source to provide the solution to the therapeutic environment at a predetermined rate over time.

17. The system of claim 14, further comprising a processor operatively coupled to the negative-pressure source and the positive-pressure source to provide negative pressure to the therapeutic environment prior to providing the solution to the therapeutic environment.

18. The system of claim 14, further comprising a processor operatively coupled to the negative-pressure source and the positive-pressure source to provide negative pressure to the therapeutic environment while providing the solution to the therapeutic environment.

19. A pressure switch for controlling application of negative pressure to dressing disposed adjacent a tissue site, comprising:
a body having a base, sidewalls extending from the base to an open end, and an inlet coupled to the dressing and forming a passage through the body;
a diaphragm closing the open end of the sidewalls and forming a vacuum chamber with the body, wherein the inlet fluidly couples the vacuum chamber and the dressing;
a valve disposed in the passage and configured to restrict the flow of gas through the passage so that a switch pressure developed in the vacuum chamber as a result of the application of negative pressure to the dressing lags a wound pressure at the tissue site, wherein the diaphragm is adapted to be operatively responsive to the switch pressure to move between a relaxed position and a compressed position as the negative pressure increases and decreases; and
a switching element coupled to the diaphragm to turn on the negative pressure in the relaxed position and turn off the negative pressure in the compressed position.

20. The pressure switch of claim 19, wherein the diaphragm comprises a center portion and a peripheral portion extending radially outwardly from the center portion to the open end of the sidewalls.

21. The pressure switch of claim 20, wherein the center portion is a membrane and the peripheral portion comprises a flexible skirt.

22. The pressure switch of claim 20, further comprising an elastic element having a first end coupled to the center portion of the diaphragm and a second end coupled to the base.

23. The pressure switch of claim 22, wherein the elastic element is a coil spring.

24. The pressure switch of claim 19, wherein the valve has an orifice with a diameter less that the diameter of the inlet.

25. The pressure switch of claim 24, wherein the diameter of the orifice is sufficiently less than the diameter of the inlet to restrict the flow of gas through the passage.

26. The pressure switch of claim 19, wherein the valve comprises a filter material that restrict the flow of gas through the passage.

27. The pressure switch of claim 19, wherein the relaxed position corresponds to a minimum target pressure selected as the wound pressure in the compressed position corresponds to a maximum target pressure selected as the wound pressure.

28. The pressure switch of claim 19, wherein the switching element is an electromechanical device.

29. The pressure switch of claim 28, wherein the switching element is a single-pole, double-throw electromechanical switch.

30. The pressure switch of claim 28, wherein the switching element comprises an actuation portion including an electrical contact having two ends wherein a first end is in a fixed position relative to the body and a second end having a contact tip, and a diaphragm portion having two electrical contacts in a fixed relationship with the diaphragm, wherein the contact tip of the actuation portion operatively contacts either one of the two electrical contacts of the diaphragm portion as the diaphragm moves between the relaxed position and the compressed position.

31. The pressure switch of claim 30, wherein the switching element further comprises a switching module that provides a first switching signal and a second switching signal in response to an electrical connection with either one of the two electrical contacts of the diaphragm portion to turn on and off the negative pressure.

32. The pressure switch of claim 28, wherein the switching element is a cantilever-spring electromechanical switch.

33. The pressure switch of claim 28, wherein the switching element comprises an actuation portion including a cantilever spring having two ends wherein a first end is in a fixed position relative to the body and a second end having a contact tip on one side and an insulator node on the other side, and a diaphragm portion having one electrical contact in a fixed relationship with the diaphragm, wherein the contact tip of the actuation portion alternately contacts the electrical contact of the diaphragm portion as the diaphragm moves between the relaxed position and the compressed position.

34. The pressure switch of claim 33, wherein the switching element further comprises a switching module that provides a first switching signal and a second switching signal in response to an electrical connection alternately with the electrical contact of the diaphragm portion to turn on and off the negative pressure.

35. The pressure switch of claim 28, wherein the switching element is an opposing-spring electromechanical switch.

36. The pressure switch of claim 28, wherein the switching element comprises an actuation portion including a latching spring and a lever in a fixed position relative to the body, the lever having a first end mechanically coupled to the latching spring and a second end having a contact tip on one side and an insulator node on the other side, and a diaphragm portion having one electrical contact in a fixed relationship with the diaphragm, wherein the contact tip of the actuation portion alternately contacts the electrical contact of the diaphragm portion as the diaphragm moves between the relaxed position and the compressed position.

37. The pressure switch of claim 36, wherein the switching element further comprises a switching module that provides a first switching signal and a second switching signal in response to an electrical connection alternately with the electrical contact of the diaphragm portion to turn on and off the negative pressure.

38. The pressure switch of claim 28, wherein the switching element is a magnetic electromechanical switch.

39. The pressure switch of claim 28, wherein the switching element comprises an actuation portion including a cantilever spring having a first end is in a fixed position relative to the body and a second end having a ferrous contact, and a diaphragm portion including a cantilever spring having a first end in a fixed position relative to the body and a second end having a magnetic contact that is also electrically conductive and in a fixed relationship with the diaphragm, wherein the ferrous contact of the actuation portion alternately contacts the magnetic contact of the diaphragm portion as the diaphragm moves between the relaxed position and the compressed position.

40. The pressure switch of claim 39, wherein the switching element further comprises a switching module that provides a first switching signal and a second switching signal in response to an electrical connection alternately between the ferrous contact and the magnetic contact to turn on and off the negative pressure.

41. A method for controlling application of negative pressure to dressing disposed adjacent a tissue site, comprising:
    positioning a dressing including a tissue interface for distributing negative pressure to the tissue site in contact with the tissue site;
    coupling a pressure switch to the dressing, the pressure switch having a vacuum chamber and an inlet valve configured to restrict the flow of gas into the vacuum chamber when negative pressure is provided to the tissue interface to develop a switch pressure in the vacuum chamber, wherein the pressure switch operatively responds to the switch pressure to move between a relaxed position and a compressed position as the negative pressure increases and decreases;
    providing negative pressure to the tissue interface to generate a wound pressure at the tissue site;
    receiving the negative pressure from the dressing into the vacuum chamber of the pressure switch wherein the switch pressure lags the wound pressure; and
    turning on the negative pressure when the pressure switch is in the relaxed position and turning off the negative pressure when the pressure switch is in the compressed position.

42. The method of claim 41, further comprising selecting a minimum target pressure as the wound pressure corresponding to the relaxed position and a maximum target pressure as the wound pressure corresponding to the compressed position.

43. The method of claim 42, further comprising inserting an elastic element into the vacuum chamber to increase the maximum target pressure and decrease the minimum target pressure.

\* \* \* \* \*